(12) United States Patent
Boyd et al.

(10) Patent No.: US 7,037,662 B1
(45) Date of Patent: May 2, 2006

(54) RECEPTOR-LIGAND SYSTEM AND ASSAY

(76) Inventors: Andrew Wallace Boyd, 110 Kitchener Road, Ascot, Queensland, 4007 (AU); Mirella Dottori, 204 Melville Road, Pascoe Vale South, Victoria, 3004 (AU); Martin Lackmann, c/-Ludwig Institute for Cancer Research, Melbourne Tumour Biology Branch, Royal Melbourne Hospital, Royal Parade, Parkville, Victoria, 3050 (AU)

( * ) Notice: Subject to any disclaimer, the term of this patent is extended or adjusted under 35 U.S.C. 154(b) by 0 days.

(21) Appl. No.: 09/104,340

(22) Filed: Jun. 25, 1998

(30) Foreign Application Priority Data

Jun. 25, 1997 (AU) ............................................. PO7549

(51) Int. Cl.
*G01N 33/50* (2006.01)
*C07K 14/00* (2006.01)
*C12N 15/00* (2006.01)
*C07H 21/04* (2006.01)

(52) U.S. Cl. .................... 435/7.1; 435/7.2; 435/7.21; 435/69.1; 435/70.1; 435/172.3; 435/235.1; 435/325; 435/375; 435/320.1; 530/300; 530/350; 536/23.1; 536/23.5

(58) Field of Classification Search ................... 435/7.1, 435/69.1, 70.1, 7.2, 7.21, 172.3, 235.1, 325, 435/375, 320.1; 530/350, 300; 536/23.1, 536/23.5
See application file for complete search history.

(56) References Cited

U.S. PATENT DOCUMENTS

| | | | | |
|---|---|---|---|---|
| 5,457,048 A | * | 10/1995 | Pasquale et al. | 435/252.3 |
| 5,635,177 A | * | 6/1997 | Bennett et al. | 424/143.1 |
| 5,674,691 A | * | 10/1997 | Boyd et al. | 435/7.2 |
| 5,738,844 A | * | 4/1998 | Beckmann et al. | 424/85.1 |
| 5,814,479 A | * | 9/1998 | Zhou et al. | 435/69.1 |
| 5,843,749 A | * | 12/1998 | Maisonpierre et al. | 435/194 |
| 5,864,020 A | * | 1/1999 | Bennett et al. | 530/388.24 |

FOREIGN PATENT DOCUMENTS

WO    WO 93/00425    1/1993

OTHER PUBLICATIONS

George et al., Current Methods in Sequence Comparison and Analysis, Macromolecular Sequencing and Synthesis, Selected Methods asd Applications. Edited by David H. Schlesinger, Alan R. Liss, In., New York. pp. 124–149, 1988.*
Andrew W. Boyd, Larry D. Ward, Ian P. Wicks, Richard J. Simpson, Evelyn Salvaris, Andrew Wilks, Karen Welch, Maureen Loudovaris, Steven Rockman, Inese Busmanis; *Isolation and Characterization of a Novel Receptor–type Protein Tyrosine Kinase (hek) from a Human Pre–B Cell Line; The Journal of Biological Chemistry*; vol. 267, No. 5, Feb. 15, 1992; pp. 3262–3267.
I. P. Wicks, D. Wilkinson, E. Salvaris, A.W. Boyd; *Molecular Cloning of HEK, the Gene Encoding a Receptor Tyrosine Kinase Expressed by Human Lymphoid Tumor Cell Lines; Proc. Natl. Acad. Sci.*, vol. 89, Mar. 1992, pp. 1611–1615.
Ian P. Wicks, Naras M. Lapsys, Elizabeth Baker, Lynda J. Campbell, Andrew W. Boyd, Grant R. Sutherland; *Localization of a Human Receptor Tyrosine Kinase (ETK1) to Chromosome Region 3p11.2; Genomics*; vol. 19, 1994, pp. 38–41.

* cited by examiner

*Primary Examiner*—Gary Kunz
*Assistant Examiner*—Nirmal S. Basi
(74) *Attorney, Agent, or Firm*—Knobbe Martens Olson & Bear LLP

(57) ABSTRACT

An Eph family RTK (receptor tyrosine kinase) ligand-binding domain as well as a method of identifying Eph family RTK agonists or antagonist. The ligand-binding domain is suitably encoded by exon III of a gone encoding the RTK of the Eph family and may additionally include an amino acid sequence encoded by exon II of the gene. The ligand-binding domain may be a polypeptide having amino acids 57–271 of the sequence shown in FIG. 1.

7 Claims, 9 Drawing Sheets

```
                                                ATG GAT TGT CAG CTC
                                                Met Asp Cys Gln Leu
                                                 1                5
TCC ATC CTC CTC CTT CTC AGC TGC TCT GTT CTC GAC AGC TTC GGG GAA
Ser Ile Leu Leu Leu Leu Ser Cys Ser Val Leu Asp Ser Phe Gly Glu
             10                  15                          20
CTG ATT CCG CAG CCT TCC AAT GAA GTC AAT CTA CTG GAT TCA AAA ACA
Leu Ile Pro Gln Pro Ser Asn Glu Val Asn Leu Leu Asp Ser Lys Thr
             25                  30                  35
ATT CAA GGG GAG CTG GGC TGG ATC TCT TAT CCA TCA CAT GGG TGG GAA
Ile Gln Gly Glu Leu Gly Trp Ile Ser Tyr Pro Ser His Gly Trp Glu
             40                  45                  50
GAG ATC AGT GGT GTG GAT GAA CAT TAC ACA CCC ATC AGG ACT TAC CAG
Glu Ile Ser Gly Val Asp Glu His Tyr Thr Pro Ile Arg Thr Tyr Gln
             55                  60                  65
GTG TGC AAT GTC ATG GAC CAC AGT CAA AAC AAT TGG CTG AGA ACA AAC
Val Cys Asn Val Met Asp His Ser Gln Asn Asn Trp Leu Arg Thr Asn
 70                  75                  80                  85
TGG GTC CCC AGG AAC TCA GCT CAG AAG ATT TAT GTG GAG CTC AAG TTC
Trp Val Pro Arg Asn Ser Ala Gln Lys Ile Tyr Val Glu Leu Lys Phe
             90                  95                     100
ACT CTA CGA GAC TGC AAT AGC ATT CCA TTG GTT TTA GGA ACT TGC AAG
Thr Leu Arg Asp Cys Asn Ser Ile Pro Leu Val Leu Gly Thr Cys Lys
             105                 110                 115
GAG ACA TTC AAC CTG TAC TAC ATG GAG TCT GAT GAT GAT CAT GGG GTG
Glu Thr Phe Asn Leu Tyr Tyr Met Glu Ser Asp Asp Asp His Gly Val
             120                 125                 130
AAA TTT CGA GAG CAT CAG TTT ACA AAG ATT GAC ACC ATT GCA GCT GAT
Lys Phe Arg Glu His Gln Phe Thr Lys Ile Asp Thr Ile Ala Ala Asp
             135                 140                 145
GAA AGT TTC ACT CAA ATG GAT CTT GGG GAC CGT ATT CTG AAG CTC AAC
Glu Ser Phe Thr Gln Met Asp Leu Gly Asp Arg Ile Leu Lys Leu Asn
150                  155                 160                 165
ACT GAG ATT AGA GAA GTA GGT CCT GTC AAC AAG AAG GGA TTT TAT TTG
Thr Glu Ile Arg Glu Val Gly Pro Val Asn Lys Lys Gly Phe Tyr Leu
             170                 175                 180
GCA TTT CAA GAT GTT GGT GCT TGT GTT GCC TTG GTG TCT GTG AGA GTA
Ala Phe Gln Asp Val Gly Ala Cys Val Ala Leu Val Ser Val Arg Val
             185                 190                 195
TAC TTC AAA AAG TGC CCA TTT ACA GTG AAG AAT CTG GCT ATG TTT CCA
Tyr Phe Lys Lys Cys Pro Phe Thr Val Lys Asn Leu Ala Met Phe Pro
             200                 205                 210
GAC ACG GTA CCC ATG GAC TCC CAG TCC CTG GTG GAG GTT AGA GGG TCT
Asp Thr Val Pro Met Asp Ser Gln Ser Leu Val Glu Val Arg Gly Ser
             215                 220                 225
TGT GTC AAC AAT TCT AAG GAG GAA GAT CCT CCA AGG ATG TAC TGC AGT
Cys Val Asn Asn Ser Lys Glu Glu Asp Pro Pro Arg Met Tyr Cys Ser
230                  235                 240                 245
ACA GAA GGC GAA TGG CTT GTA CCC ATT GGC AAG TGT TCC TGC AAT GCT
Thr Glu Gly Glu Trp Leu Val Pro Ile Gly Lys Cys Ser Cys Asn Ala
             250                 255                 260
GGC TAT GAA GAA AGA GGT TTT ATG TGC CAA
Gly Tyr Glu Glu Arg Gly Phe Met Cys Gln
             265                 270
```

*FIG. 1*

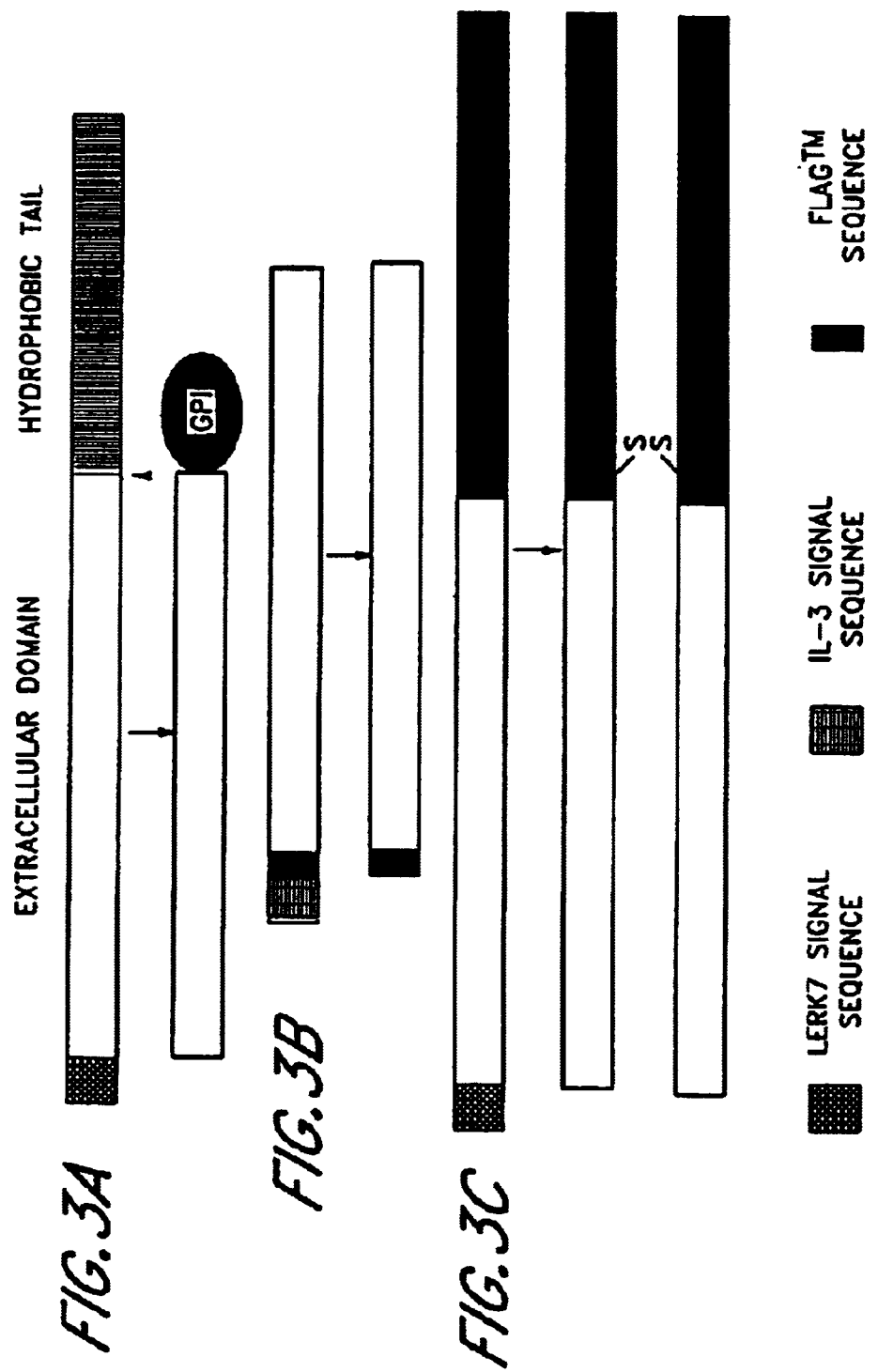

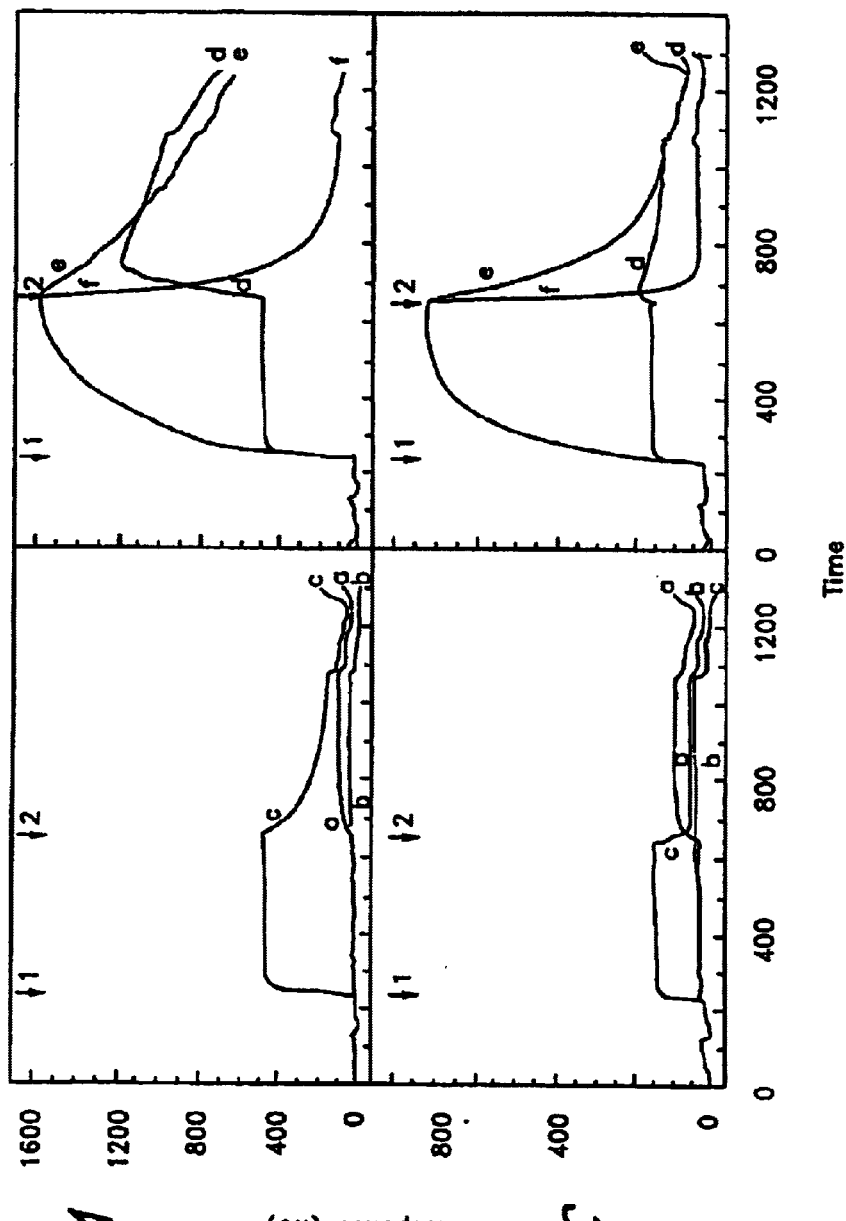

RECEPTOR-LIGAND SYSTEM AND ASSAY

FIELD OF THE INVENTION

This invention relates to the Eph family of receptor tyrosine kinases, to the high-affinity ligand-binding site of such receptors, and to methods whereby Eph receptor agonists and antagonists may be identified. In particular, the invention relates to the Eph family receptor HEK. Because of the highly conserved nature of the receptor tyrosine kinases of the Eph family, the methods of the invention are applicable to other members of this family such as EPH, ECK and ERK. Generally, Eph receptor tyrosine kinases are involved in embryonic development of the brain and nervous system, leukaemias and solid tumors, and may have a role in metastasis.

BACKGROUND OF THE INVENTION

Increasing interest in understanding the molecular basis of tissue modeling and patterning processes in vertebrate development has led to the identification of protein families which direct cell movement in embryogenesis (reviewed by Bonhoeffer & Sanes, 1995, Curr. Opin. Neumbiol. 5 1–5). Apart from members of the fibroblast growth factor (FGF) and transforming growth factor beta (TOF-β) families, which are involved in mesoderm induction and patterning (Green & Smith, 1991, Trends in Genetics 7 245–250), proteins of the netrin, semaphorin and collapsin families are thought to control axon guidance and neural pathfinding (Kennedy & Tessier-Lavigne, 1995, Current Opinion in Neurobiology 5 83–90; Müller et al., 1996, Current Opinion in Genetics and Development 6 469–474).

Such growth factors and their cell surface receptors, as well as many other types of receptor-ligand pairs, have characteristic mechanisms for transducing the ligand-receptor binding effect into intracellular changes.

One major receptor type is the receptor protein-tyrosine kinase (RTK) family, the members of which include intracellular tyrosine kinase domains which are activated in response to ligand simulation, resulting in autophosphorylation of certain receptor tyrosine residues. The phosphorylated tyrosines in turn bind to and activate signaling molecules, thereby activating an intracellular signaling cascade.

Over 14 distinct groups of RTKs are known, and of these the largest group is the "Eph" family, which until comparatively recently were "orphan" receptors for which no ligand had been identified. However, the Eph family ligands are now known to represent a family of glycosyl phosphatidylinositol (GPI)-linked or transmembrane molecules.

Among RTKs which are implicated in the regulation of developmental patterning events (Pawson and Bemstein, 1990, Trends Genet. 6 350–356), members of the Eph-family RTKs have been linked to neurogenesis (Müller et al., 1996, supra; Tessier-Lavigne, M., 1995 Cell 82 345–348: Pandey et al., 1995 5 986–989; Nieto, M. A. 1996, 17 1039–1048) initially due to their spatially-restricted expression patterns during the development of the vertebrate nervous system (reviewed by Friedman & O'Leary, 1996, Current Opinion in Neurobiology 6 127–133). The characterisation of the expression patterns together with functional studies of Eph receptors has, in several cases, confirmed significant roles for Eph signaling in axon guidance, in particular, during the development of the retinotectal projection map (Cheng & Flanagan, 1994, Cell 79 157–168; Chang et al., 1995, Cell 82 371–381; Drescher, U., 1995, Cell 82 359–370; Winslow, et al. 1995, Neuron 14 973–981; Tessier-Lavigne, 1995, supra; Brennan et al., 1997, Development 124 655–664).

The results of studies utilizing overexpression of some family members including HEK, EPH, ERK and ECK in tumour-derived cell lines, tumour specimens and transfected cells implicates these receptors in oncogenesis (Hiral et al., 1989, Science 238 1717–20; Boyd et al., 1992, J. Biol. Chem. 267(5) 3262–7: Maru et al., 1990; Andres et al., 1994, Oncogene 9 1461–7).

HEK was first identified on the cell surface of a pre-B acute lymphoblastic leukemia cell line, LK63, using the III-A4 monoclonal antibody (Boyd et at., 1992, supra). Immunofluorescence studies with III-A4 revealed expression of HEK in blood samples from patients with acute leukemia, but not in normal adult tissues or blood cells (Boyd et al., 1992, supra; Wicks et al., 1992, Proc. Natl. Acad. Sci. (USA) 89(5) 1611–5).

A cDNA encoding HEK has been obtained and the nucleotide sequence of the entire coding region deduced as reported in Wicks et al., 1992, Proc. Natl. Acad. Sci USA (which is herein incorporated by reference), and in WO93/00425 (which is herein incorporated by reference).

In embryos, the expression patterns of the murine and chicken HEK homologues MEK 4 and CEK 4, and their recently identified respective ligands ELF1 and RAGS, suggest a role in the development of the retinotectal projection map. A soluble HEK ligand from human placenta conditioned medium has been identified using a biosensor-based affinity detection approach (Lackmann et al., 1995). The HEK ligand was identified by sequence homology as a soluble form of AL-1 (Winslow at al., 1995, Neuron 14 973–981), a member of the family of ligands for EPH Related Kinases (LERKS: Bohme et at., 1996, J. Biol. Chem. 271 24727–24752; Cerreti et al., 1996, Genomics 35 376–379), which for consistency with other members will hereinafter be referred to as LERK 7. This family of transmembrane or membrane-associated proteins were isolated as potential ligands for EPH-like RTKs through their interactions with recombinant EPH receptor family exodomains (Winslow et al. 1994: Beckmann et al., 1994, Embo Journal. 13 3757–62; Shao et al., 1995, Journal of Biological Chemistry 270 3467–70; Brambilia et al., 1995, Embo Journal 14 3116–3126).

Extremely high interspecies sequence similarities of the known Eph family members suggests that these receptors have evolutionarily conserved functions, but little is known about the actual protein structures or about the structure/function relationships between Eph-like receptors and their ligands. Typically, and as is the case with HEK, Eph RTKs have an exodomain which includes an N-terminal cysteine-rich region, the outer portion of which has been described as immunoglobulin-like (Ig-like), and two fibronectin ill regions (Pandey et at., 1995, Journal of Biological Chemistry 270 19201–19204; Tuzi & Gullick, 1994, British Journal of Cancer 69 417–421; Henkemeyer, M., 1994, Oncogene 9 1001–1014). Extensive crossreactivity of Eph receptor/ligand interactions has been observed with divalent receptor (ligand) fusion proteins containing the Fc domain of human IgG 1 (Beckmann et al., 1994, supra; Davis et al., 1994, Science 266 816–819; Pandey et al., 1994, Journal of Biological Chemistry 269 30154–30157; Cerretti et al. 1995, Molecular Immunology 32 1197–1205; Pandey et oh, 1995, Current Biology 5 986–989; Brambilla St al., 1995, supra).

All of the known ligands exist as membrane-associated forms, and dependence of receptor activation on membrane bound or oligomerised ligands (Winslow et al., 1995, supra; Davis et al., 1994, supra) was reported for most members of the Eph-like receptor and ligand families. The apparent receptor/ligand promiscuity of various receptors and ligands monitored with receptor or ligand Fc fusion constructs suggested that Eph family RTKs could be separated into two redundant sub-classes, based on affinity for transmembrane of GPI-linked respectively. Together with their overlapping expression patterns, this led to the formulation of a model in which promiscuous interactions within subclasses mediates formation of spatial boundaries and patterning events during development (Gale et at., 1996, Neuron 17 9–19).

This reported redundancy is at odds with several studies which demonstrate specialised functions of the homologous RTKs MEK4/CEK4/RTK2 and their corresponding ligands ELF1/RAGS/zEphL4 during the development of the retino-teotal projection map in mouse, chicken and zebrafish (Cheng et at., 1995, Cell 82 371–381; Drescher et al., 1995, Cell 82 359–370, Nakamoto et al., 1996, Cell 86 755–766; Brennan et at., 1997, Development 124 655–664).

OBJET OF THE INVENTION

The present inventors have realized that in order to determine the specific function of each Eph RTK, it is essential that the nature of the ligand-receptor interaction relevant to each Eph family RTK be resolved.

With this realization in mind, the present inventors have identified LERK7 as the preferred high-affinity ligand for HEK, and thereby located a domain within HEK which is responsible for binding the high affinity ligand. The previously-mentioned high level of sequence similarity between EpH-family RTKs suggests that similarly located ligand-binding domains exist in all Eph family RTKs.

It is therefore an object of the invention to provide an Eph family RTK ligand-binding domain.

It is a further object of the invention to provide a method of identifying Eph family RTK agonists or antagonists.

DISCLOSURE OF INVENTION

In one aspect, the invention provides a ligand-binding domain of a receptor protein kinase (RTK) of the Eph family.

Preferably, the Eph-family RTK Is HEK.

Preferably, the ligand which binds the ligand-binding domain is LERK7.

Preferably, the ligand-binding domain comprises at least one disulphide bond involving cysteine residues corresponding to conserved cysteine residues in HEK which are selected from the group consisting of:

(i) $CYS_{71}$–$CYS_{189}$;

(ii) $CYS_{257}$–$CYS_{270}$;

(iii) $CYS_{259}$–$CYS_{270}$;

(iv) $CYS_{305}$–$CYS_{322}$; and (v) $CYS_{352}$–$CYS_{385}$.

Preferably, the ligand-binding domain is encoded by exon III of a gene encoding said RTK of the Eph family.

Preferably, the ligand-binding domain additionally includes an amino acid sequence encoded by exon II of said gene.

Most preferably, the ligand-binding domain includes an amino acid sequence encoded by axon I, axon II and exon III of said gene.

Furthermore, and as will be discussed hereinafter, a ligand-binding domain comprising an amino acid sequence encoded by exon I, exon II and exon III of said gene is particularly useful for recombinant expression.

Preferably, said ligand-binding domain is a polypeptide having amino acids 52–271 of the sequence shown in FIG 1 (SEQ ID NO:1).

Preferably, said ligand-binding domain polypeptide further includes one or more of amino acids 30–51 of the sequence shown in FIG. 1 (SEQ ID NO:2).

Preferably, said ligand-binding domain polypeptide further includes one or more of amino acid residues 1–29 of the sequence shown in FIG. 1 (SEQ ID NO:3).

As previously mentioned, a ligand-binding domain of an Eph-family RTK which is particularly useful for recombinant expression consists of amino adds 1–271 of the sequence shown in FIG. 1 (SEQ ID NO:4).

It will be appreciated that the amino acid sequence shown in FIG. 1 (SEQ ID NO:4), corresponds to that encoded by exons I, II and III of the human HEK gene.

In this regard, and as will be described hereinafter, exon III encodes amino acids which appear to be necessary for ligand binding by Eph family RTKs. However, it is also clear that amino acid sequences flanking the exon III-encoded sequence may also form part of the ligand-binding domain, perhaps by contributing to correct folding or other structural requirements of the ligand-binding domain. The functional importance of the axon III-encoded amino acid sequence will also be demonstrated hereinafter.

In a second aspect, the invention provides a polynucleotide sequence as shown in FIG. 1 (SEQ ID NO:5), wherein:

(i) nucleotides 1–87 correspond to exon I of the HEK gene (SEQ ID NO:6);

(ii) nucleotides 88–153 correspond to exon II of the HEK gene (SEQ ID NO:7); and (iii) nucleotides 154–813 correspond to exon III of the HEK gene (SEQ ID NO:8).

The present invention also provides homologs of the polynucleotide sequence of the invention, which homologs include:

(1) all polynucleotide sequences encoding polypeptides of the invention; and (2) all polynucleotide sequences encoding subsequences of polypeptides of the invention.

As used herein, "sub-sequences of polypeptides of the invention" are polypeptides of the invention which have one or more amino acid sequence deletions, but which retain the functional characteristics of the polypeptide of the invention.

In this regard, a skilled addressee would also realize that advantage can be taken of codon sequence redundancy so se, to incorporate changes in a nucleotide sequence without affecting the encoded amino acid sequence.

Furthermore, a skilled addressee would be aware that one or more nucleotides of the polynucleotide sequences of the invention could be substituted so as to produce one or more conservative amino acid changes that do not alter the functional characteristics of the polypeptides of the invention.

Thus, the homologs of the invention include altered polynucleotide sequences which encode polypeptides with the same functional characteristics as the polypeptides of the invention.

The polynucleotide sequence homologs of the invention further comprise polynucleotide sequences that hybridize with polynucleotide sequences of the invention under substantially stringent conditions. Suitable hybridization conditions will be discussed hereinafter.

"Hybridization" is used here to denote the pairing of complementary bases of distinct polynucleotide sequences to produce a DNA—DNA hybrid, a DNA-RNA hybrid, or an RNA—RNA hybrid according to base-pairing rules.

In DNA, complementary bases are:
(i) A and T; and
(ii) C and G.

In RNA, complementary bases are:
(i) A and U; and
(ii) C and G.

In DNA-RNA hybrids, complementary bases are:
(i) A and T;
(ii) A and U; and
(iii) C and G.

Typically, substantially complementary polynucleotide sequences are identified by blotting techniques that include a step whereby polynucleotides are immobilized on a matrix (preferably a synthetic membrane such as nitrocellulose), a hybridization step, a washing step and a detection step.

Southern blotting is used to identify a complementary DNA sequence; Northern blotting is used to identify a complementary RNA sequence. Dot blotting and slot blotting can be used to identify complementary DNA/DNA, DNA/RNA or RNA/RNA polynucleotide sequences. Such techniques are well known by those skilled in the art, and have been described in CURRENT PROTOCOLS IN MOLECULAR BIOLOGY (Eds. Ausubel et al., John Wiley & Sons Inc 1995) at pages 2.9.1 through 2.9.20. According to such methods, Southern blotting involves separating DNA molecules according to size by gel electrophoresis, transferring the size-separated DNA to a synthetic membrane, and hybridizing the membrane bound DNA to a complementary polynucleotide sequence labeled radioactively, enzymatically or fluorochromatically. In dot blotting and slot blotting, DNA samples are directly applied to a synthetic membrane prior to hybridization as above.

An alternative blotting step is used when identifying complementary polynucleotide sequences in a cDNA or genomic DNA library, such as through the process of plaque or colony hybridization. A typical example of this procedure is described, in Sambrook et al., MOLECULAR CLONING: A LABORATORY MANUAL 2nd Ed (Cold Spring Harbour Press 1989) Chapters 8–12, which is herein incorporated by reference.

A skilled addressee will recognize that a number of factors influence hybridization, and that these factors can be manipulated to optimize the specificity of the hybridization.

Maximum hybridization typically occurs at about 20' to 25' below the $T_m$ for formation of a DNA—DNA hybrid. Maximum hybridization typically occurs at about 10' to 15' below the $T_m$ for a DNA—RNA hybrid.

It is well known in the art that the $T_m$ Is the melting temperature, or temperature at which two complementary polynucleotide sequences dissociate. Methods for estimating $T_m$ are well known in the art (see CURRENT PROTOCOLS IN MOLECULAR BIOLOGY supra at page 2.10.8).

A commonly used empirical formula for calculating DNA $T_m$ is:

$$T_m = 81.5° C. + 16.6(\log M) + 0.41(\% \ G+C) - 0.61(\% \ \text{formamide}) - 500/L$$

where M=molarity of monovalent cations
and L=sequence length

The specific activity of radioactively labeled polynucleotide sequence should typically be at least $10^5$ dpm/μg to provide a detectable signal. A polynucleotide sequence radiolabeled to a specific activity in the order of $10^9$ dpm/μg can detect approximately 0.5 pg of DNA. It is well known in the art that sufficient DNA must be immobilized on the membrane to permit detection. It is desirable to have excess immobilized DNA, usually 10 μg. Adding an inert polymer such as 10% (w/v) dextran sulfate (MW 500,000) or polyethylene glycol 60000 during hybridization can also increase the sensitivity of hybridization (see Ausubel et al., supra at 2.10.10).

To achieve meaningful results from hybridization between a polynucleotide sequence immobilized on a membrane and a labeled polynucleotide sequence, a sufficient amount of the labeled polynucleotide sequence must be hybridized to the immobilized polynucleotide sequence following washing. Washing ensures that the labeled polynucleotide sequence is hybridized only to the immobilized polynucleotide sequences with a desired degree of complementarity to the labeled polynucleotide sequence.

"Stringency" as used herein, refers to the temperature and ionic strength conditions, and presence or absence of certain organic solvents, during hybridization. The higher the stringency, the higher will be the degree of complementarity between the immobilized polynucleotide sequences and the labeled polynucleotide sequence.

"Stringent conditions" designates those conditions under which only polynucleotide sequences having a high frequency of complementary bases will hybridize, and remain hybridized during washing.

For a detailed example of stringent conditions, see CURRENT PROTOCOLS IN MOLECULAR BIOLOGY supra at pages 2.10.1 to 2.10.16, and Sambrook et al in MOLECULAR CLONING, A LABORATORY MANUAL (Cold Spring Harbour Press, 1989) at sections 1.101 to 1.104, which are hereby incorporated by reference.

Methods for detecting labeled polynucleotides hybridized to an immobilized polynucleotide are well known to practitioners in the art. Such methods include autoradiography, chemiluminescent, fluorescent and calorimetric detection.

It is also contemplated that polynucleotide sequence homologs may be obtained using polynucleotide sequence amplification techniques.

In this regard, the polynucleotide sequence homologs of the invention may be prepared according to the following procedure:

(i) designing primers based on sub-sequences of a polynucleotide sequence of the invention; and (ii) using said primers to amplify, via polynucleotide sequence amplification techniques, one or more fragments from a polynucleotide extract.

By "fragment" is meant a DNA product generated by polynucleotide sequence amplification techniques.

As used herein, "sub-sequences of polynucleotide sequences" are sequences of nucleotides contained within the polynucleotide sequence of the invention.

In this regard, it will also be appreciated that said primers may be degenerate, in which case nucleotide sequences thereof will be determined according to an amino acid sequence encoded thereby. That is, advantage may be taken of codon sequence redundancy to design said degenerate primers so that polynucleotide sequence homologs which have non-conserved nucleotide sequence(s) may be amplified according to this method.

Suitable polynucleotide sequence amplification techniques are well known to the skilled addressee, and include polymerase chain reaction (PCR), strand displacement amplification (SDA) and rolling circle replication (RCR).

The polynucleotide extract may be in the form of a cDNA or genomic library. In this regard, the cDNA or genomic library may be derived from a eukaryote, including mammals such as humans or mice. Such libraries may comprise genomic DNA or cDNA ligated into vectors such as λ FIX II or λ DASH II, as will be described hereinafter.

Alternatively, said polynucleotide extract could be an mRNA extract obtained from cells or tissues which has been reverse transcribed to cDNA.

The polypeptides of the invention also include within their scope homologs, and sub-sequences thereof as previously defined.

A polypeptide homolog is a polypeptide of the invention with an altered amino add sequence, such as through conservative amino acid substitution(s), but with unaltered functional characteristics.

A recombinant polypeptide of the invention may be prepared by a procedure comprising the steps of:
  (i) ligating a polynucleotide sequence of the invention into a suitable expression vector to form an expression construct;
  (ii) transfecting or transforming a suitable host cell with said expression construct;
  (iii) expressing said polypeptide of the invention; and
  (iv) isolating said polypeptide of the invention.

It will be understood that this procedure is applicable to polypeptide sequences of the invention, homologs and subsequences thereof.

The expression construct comprises an expression vector, as is well known in the art, and a polynucleotide sequence of the invention which encodes a polypeptide of the invention, wherein the polynucleotide sequence of the invention is operably linked to one or more regulatory nucleotide sequences present in the expression vector (such as a promoter, terminator and polyadenylation sequence) that will induce expression of the polypeptide of the invention.

Both constitutive and inducible promoters may be useful adjuncts for expression of polypeptides according to the invention. An expression vector according to the invention may be a plasmid cloning vector suitable for either prokaryotic or eukaryotic expression. Such vectors are well known to those skilled in the art.

A preferred eukaryotic expression vector which provides constitutive expression is pEFBOS, as will be described hereinafter.

In light of the foregoing, it will also be realized by those skilled in the art that the expression vector and the host cell used will be interdependent.

Preferred host cells for eukaryotic expression are Chinese Hamster Ovary (CHO) calls and COS 7 coils, as will be described hereinafter.

An expression construct may also include a fusion partner sequence (usually provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate the polynucleotide sequence of the invention into the expression vector so that the translational reading frames of the fusion partner and the polynucleotide sequence of the invention coincide.

Well known examples of fusion partners are glutathione-S-transferase (GST), Fc portion of human $IgG_1$, maltose binding protein (MBP) and hexahistidine ($HIS_6$), which are particularly useful for isolation of the fusion polypeptide of the invention by affinity chromatography. For the purposes of fusion polypeptide purification by affinity chromatography, relevant matrices for affinity chromatography are glutathione-, amylose-, and nickel- or cobalt-conjugated resins respectively.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention. Flow cytometric methods such es fluorescence activated cell sorting (FACS) are particularly useful in this latter application.

Preferably, the fusion partners also have protease cleavage sites, such as for Factor $X_a$ or Thrombin, which allow the relevant protease to partially digest the fusion polypeptide of the invention end thereby liberate the recombinant polypeptide of the invention therefrom. The liberated polypeptide can then be isolated from the fusion partner by subsequent chromotagraphic separation.

Fusion partners according to the invention also include within their scope "epitope tags", which are usually short peptide sequences for which a specific antibody is available. Well known examples of epitope tags for which specific monoclonal antibodies are readily available include c-myc, influenza virus haemagglutinin and FLAG tags.

Preferably, the FLAG tag is used as an epitope tag with polypeptides of the invention. This epitope tag is preferably recognized by the anti-FLAG M2 monoclonal antibody (mAb). As will be demonstrated hereinafter, the presence of a FLAG-epitope does not appreciably alter the biological interaction between HEK and its high-affinity ligand LERK 7.

It will also be appreciated that polypeptides of the invention, homologs and subsequences thereof may be prepared by chemical synthesis, rather than by recombinant DNA methods.

Applicable methods of chemical synthesis are well known in the art, and it is customary for such methods to be automated and readily available to the skilled person. This approach is particularly relevant to the preparation of peptides, for example corresponding to subsequences of polypeptides of the invention. Suitable polypeptide synthesis procedures are described in detail in Chapter 18 of CURRENT PROTOCOLS IN PROTEIN SCIENCE, Collgan et al. Eds (John Wiley & Sons). Also, chemical synthesis of a peptide consisting of amino acid residues 1–31 of HEK will be described hereinafter.

In a third aspect, the invention provides a method of identifying a molecule which binds an Eph RTK, which method includes the steps of:
  (i) combining a sample suspected of containing said molecule and at least a ligand-binding domain of an Eph family RTK; and
  (ii) determining if the molecule is present in the sample by measuring binding of said molecule to the ligand-binding domain.

The ligand-binding domain may have additional amino acid sequences or polypeptide domains. For example, it may be advantageous for said at least a ligand binding domain to have amino acids which are involved in dimerization of said Eph family RTK.

As used herein "sample" refers to any material which may potentially contain said molecule. It will be appreciated that said molecule could be a high-affinity ligand such as LERK7, in which case the method according to this aspect of the invention is useful for diagnostically detecting the ligand in samples such as body fluids, cell extracts, serum and the like.

Alternatively, this method is useful for identifying hitherto unknown Eph family RTK-binding molecules which mimic ligands such as LERK7. Such molecular mimics are hereinafter referred to as "agonists".

In a fourth aspect, the invention provides a method of identifying a molecule which competes with binding of a ligand to at least a ligand-binding domain of an Eph family RTK, which method includes the steps of:
(i) combining a sample suspected of containing the molecule, a ligand and at least a ligand-binding domain of an Eph family RTK; and
(ii) determining if the molecule is present in the sample by measuring whether the molecule competes with said ligand for binding to said ligand-binding domain.

It will be appreciated that the method according to the third and fourth aspects of the invention may be suitable for identifying molecules which interfere with binding between Eph family RTKs and their ligands. Such molecules are hereinafter referred to as "antagonists".

It will be appreciated that there are numerous binding assays available to the skilled addressee which are suitable according to the methods of the third and fourth aspects.

Such assays include radioligand binding assays, affinity chromatography-based assays, equilibrium sedimentation analysis, and sensor chip-based assays such as using the BIAcore system.

Preferably, detection of agonists and/or antagonists is performed using assays wherein either the Eph family RTK ligand-binding domain or said ligand is immobilized on a solid support such as a microtitre plate-well, bead (e.g. CNBR-activated sepharose) or a sensor chip such as is used with the BIACore system.

Advantageously, the method according to the third and fourth aspects of the invention utilizes said BIACore system. The BIACore system provides an extremely sensitive and efficient technique which is well known to the skilled person. The operation of the BAICore system will be described in detail hereinafter.

In a fifth aspect, the present invention provides agonists and/or antagonists of Eph family RTKs.

In this regard, it will be appreciated that the ligand-binding domain of the present invention may itself be an antagonist by virtue of its ability to compete with Eph family RTKs for ligand binding.

According to this aspect, it is preferable that the ligand is LERK 7 and that said Eph family RTK is HEK.

In a sixth aspect, the invention provides a method of determining whether or not an mRNA encodes an intact Eph family RTK ligand-binding domain, which method comprises the step of introducing the mRNA into a zebrafish embryo at the one-cell, two-cell, or four-cell stage, and detecting defects, if present, in early embryogenesis in the zebrafish embryo, said defects being indicative of said mRNA encoding said intact ligand-binding domain.

Preferably the mRNA has a nucleotide sequence corresponding to the first seven exons of an Eph family RTK gene.

Preferably, the Eph family RTK is HEK.

In a seventh aspect, the invention provides a method of determining whether or not an mRNA encodes an intact ligand for an Eph family RTK ligand-binding domain, which method comprises the step of transcribing the gene to mRNA, introducing the mRNA into a zebrafish embryo at the one-cell, two-cell, or four-cell stage, and detecting defect, if present, in early embryogenesis in the zebrafish embryo, said defects being indicative of said mRNA encoding said intact ligand.

Preferably, the ligand is LERK 7.

According to the sixth and seventh aspects, it is preferred that mRNA is introduced into the embryo by microinjection into the yolk cell immediately under the blastoderm. Suitable methods for preparing mRNA will be described hereinafter.

Preferably a syndrome comprising defects involving reduced dorsal axis height form the yolk cell, disorganised anterior neuraxis, and disorganised somite boundaries is detected.

More preferably this syndrome of defects is detected in at least 50% of embryos subjected to the test.

As will be discussed in more detail hereinafter, injection of mRNA encoding LERK 7 causes defects identical to the defects caused by soluble HEK comprising the ligand-binding domain. Furthermore, co-injection of receptor and ligand mRNA achieves a partial rescue of the phenotype, demonstrating the specificity of the receptor-ligand mediated effects.

In an eighth aspect, the invention provides a method of identifying the site of functional effects of interaction between an Eph family RTK ligand-binding domain and a ligand, comprising the steps of injecting zebrafish embryos with mRNA encoding the ligand-binding domain, and subjecting the embryos to in situ hybridisation with probes to Hix-1, Paxb, Krox20 and/or MyoD, and detecting patterns of in situ hybridisation consistent with aberrant gene expression.

Preferably the Eph family RTK is HEK, and the ligand is LERK 7. Preferably the method according, to the eighth aspect is used to identify events occurring during embryogenesis.

The method according to the eighth aspect of the invention may also be useful for identifying Eph family RTK agonists and antagonists.

Eph family RTKs are associated with solid tumours such as melanoma and cancers of the colon, liver, lung, breast and prostate. Eph family RTKs play a role in metastasis possibly due their role in cell migration and tissue structure. In particular, HEK is associated with pre-B cell leukaemia and with other leukaemias. It is therefore considered that agonists and antagonists of the invention, such as LERK 7 agonists/antagonists, may be potentially useful as anti-cancer or anti-metastatic agents.

BRIEF DESCRIPTION OF THE DRAWINGS

FIG. 1: Nucleotide sequence of exon I (nucleotides 1–87 SEQ ID NOS 5 and 6), exon II (nucleotides 88–153 SEQ ID NOS 5 and 7) and exon III (nucleotides 154–813 SEQ ID NOS 5 and 8) of the HEK gene, and the deduced amino sequence. The nucleotide sequence of FIG. 1 SEQ ID NO 5 was constructed using the data in Table 1 together with the HEK cDNA sequence as shown in Wicks et al., 1992 supra and WO 93/00425 supra.

FIG. 3: Schematic comparison of native LERK7 with FLAG and Fc fusion constructs. In each case the precursor protein is depicted with an arrow leading to the final processed form. The original precursor protein is processed to remove the signal sequence and the hydrophoblo glycophosphatidyl inositol linkage sequence (cleavage site indicated by arrow head) yielding the final GPI-linked form (FIG. 3A). LERK7-FLAG is engineered to stop before the hydrophobic tail and the native N-terminal signal sequence is replaced with the IL3 signal peptide and the FLAG epitope (FIG. 3B). FIG. 3C illustrates the LERK7-Fc construct where the hydrophobic tall of the native sequence is replaced by the Fc and hinge regions of human $IgG_1$. After processing this yields the disulphide linked homodimer (Bohme et al., 1996, supra).

FIG 6: Characterisation of bivalent ligand binding by generation of ternary sHEK/LERK-FLAG/anti-FLAG M2 mAb complexes in situ. Solutions (5 μg/ml) of purified LERK 7-FLAG (panels A, B) or LERK 3-FLAG (panels C, D) with (sensorgrams e,f), or without addition (sensorgram c) of cross-linking anti-FLAG M2 mAb (5 μg/ml) were injected across an sHEK-derivatised sensor surface (1) followed by a subsequent injection (2) of buffer (sensorgrams c, e), M2 Mab (5 μg/ml, sensorgram d) or FLAG peptide (25 μg/ml, sensorgram f). For comparison, injections of buffer (1) followed (2) by M2 mAb or FLAG peptide (sensorgrams a and b, respectively) were performed in parallel experiments.

DETAILED DESCRIPTION OF THE PREFERRED EMBODIMENT

Figure 2A:
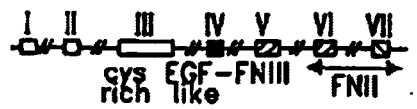
FIG. 2A: Correspondence between exon structure and subregions of the extracellular portion of Eph family RTKs.

We have now shown that monovalent ligand constructs interact with Hek with markedly different affinities, with LERK7/AL-1 being 50-fold more avid than LERK3. This suggests that these receptors do not show true redundancy, but rather use varying affinity for different, and possibly overlapping, ligand gradients for fine control of cell movement within the developing organism.

In this specification we describe studies of the exon structure of the HEK gene, particularly with regard to the exons encoding the extracellular region or exodomain of HEK end related RTKs to demonstrate a consensus structure for all these genes. Deletion mutants of the HEK exodomain were constructed based on these data and expressed protein obtained. With the elucidation of the HEK gene structure as a starting point, we exploited the specific interaction between HEK and LERK7 in a blosensor-based strategy to identify the N-terminal, exon III-encoded cysteine-rich sub-domain as a crucial part of the ligand binding domain.

These receptor exodomain constructs were analysed functionally in a dominant-negative approach by micro-injecting mRNA encoding either the full-length receptor exodomain (HEK I–VII) or the soluble ligands (LERK7), or a deletion construct of the receptor, in which the coding sequence for the ligand binding domain was absent (HEK IV–VII mRNA), into zebrafish embryos. Whereas injection of HEK I–VII mRNA and mRNA encoding soluble LERK7 had severe, dose-dependent effects on the development of the fish embryos. A phenotype comparable to non-injected control embryos was observed at moderate concentrations of injected HEK IV–VII mRNA and expression of comparable amounts of the endogenous protein.

In addition to severely impaired mid and hindbrain development, prominent effects on axis and somite formation were observed early during development (12–14 h post fertilisation), in accord with the early expression patterns of the putative zebrafish HEK homologue rtk2 (N. Holder, personal communication) starting at 80–90% epiboly (9 hpf) as reported previously by Xu et at., 1994). The defects are consistent with a failure of lateral cells to move towards the midline as part of the cell movements enacted during gastrulation. Furthermore, our results raise the possibility of an endogenous signal mediated by a LERK 7 homolog and required by lateral cells for migration towards the midline.

Our data demonstrate a pivotal role of HEK/rtk2 during early vertebrate embryogenesis, and indicate that a defined ligand/receptor interaction has critical functions at progressive developmental stages.

EXPERIMENTAL MATERIALS AND METHODS
1. Isolation and mapping of HEK genomic clones The HEK cDNA probes used to screen the human genomic libary were PCR fragments amplified from plasmids containing full length HEK cDNA. The primers used were:
probe A (spans bases 74 to 116 as described by Wicks et al., 1992, supra)
GTAGGAATTCCTCTCACTGCCCTCTGC (SEQ ID NO: 9) and
GTAGGGATCCGGCCTCCTGTTCCAG (SEQ ID NO: 10);
probe B (bases 1053 to 1124)
GTAGGAATTCCATGG CTTGTACCCGAC (SEQ ID NO: 11) end
GTAGGGATCCCATAATGCTTGCTTCTC (SEQ ID NO: 12);
probe C(bases 2 to 186)
ATGG ATGGTAACTTCTCCAG (SEQ ID NO: 13) and
TCATTGGAAGGCTGCGGAAT (SEQ ID NO: 14), and
probe D (bases 909 to 1404)
GTAGTCTAGACAAGCTTGTCGACCAGGTT (SEQ ID NO: 15) and
GTAGTCTAGATCAAGCCTGATTAGTTG TGATGC (SEQ ID NO: 16).

The mouse genomic library was screened with a MEK4 fragment isolated from a plasmid subcloned with MEK4 cDNA. The cDNA fragment spans bases 582 to 899 of the MEK4 sequence (Saijadi et al., 1991, New Biologist 3 769–778).

The genomic libraries used were human in λ FIX II vector, (Stratagene Cloning Systems, La Jolla) and mouse in λ FIX II vector (Stratagene) and DASH II vector (kindly provided by F. Kontgen, Walter and Elize Hall Institute for Medical Research, Melbourne). Approximately $10^6$ plaques from each library were plated, replica nylon membrane filters (Bio-Rad Laboratories, New York) were prehybridized at 42° C. In 50% formamide, 10× Denhardt's solution, 0.05 M Tris-Cl pH 7.5, 1.0 M NaCl, 2.24 mM tetra-sodium pyrophosphate, 1% SDS, 10% dextran sulfate and 0.1 mg/ml sheared, heat-denatured herring sperm DNA, and the filters hybridized at 42° C. for 16 hours. Washes were performed at 88° C. in 0.1×SSC, 0.1% SDS for 1 hour and in 0.1×SSC, 0.5% SDS for a further 30 minutes. Positive clones were identified by autoradiography, purified by subsequent screenings and isolated using standard methodology (Sambrook et al., 1989, supra).

Exon-intron boundaries were determined by a combination of direct DNA sequencing, PCR, restriction analyses, and Southern blotting. Direct DNA sequencing of the genomic lambda phages and subcloned plasmid was performed using the ABI 373 DNA sequencer (Applied Biosysterris, Melbourne, Australia). Sequencing and PCR primers used to characterize the HEK gene from human genomic clones were based on the HEK cDNA sequence (Wicks et al., 1992, supra).

The exons found within the mouse genomic clones were amplified by PCR using degenerate primers specific to Eph family RTKs:
GTAGGCATGCAAGGAGA C(AC)TT(CT)AACC (SEQ ID NO: 17), and
CC(AG)ATGGGNACCAGCCA(CT)TC (SEQ ID NO: 11).

The PCR products were then directly sequenced as described above using the degenerate primers.
2. Production of HEK in CHO cells Soluble HEK and N-terminally FLAG-tagged HEK were prepared from transfected Chinese Hamster ovary (CHO) cell supernatants as previously described (Lackman et al., 1996, Proc. Natl. Aced. Sci. (USA) 93 2523–7). Deletion mutants of HEK were prepared by PCR using oligos based on the exon boundaries. HEK III and HEK IV were constructed using a 5' oligonucleotide based on the N terminal sequence of the mature protein (Boyd et al., 1992, supra) with a 5' XbaI-site (GTAGTCTAGAGAACTGATTCCGCAGCCTTCCAA) (SEQ ID NO: 19) and 3' oligonucleotides based on sequences spanning exon IV (GTAGTCTAGATCATGGAGGTCGGGTACAAGC) (SEQ ID NO: 20) and exon III (GTAGTCTAGATCAAGCTTGGCACATAAAACCTC) (SEQ ID NO: 21) respectively, followed by a stop codon and an XbaI site. To construct HEK IV–VI, a 5' oligo designed to span the 5' end of exon IV with a 5' XbaI site (GTAGTCTAGACAAGCTTGTCGACCAGGTTTC) (SEQ ID NO: 22) and a 3' oligonucleotide based on the C-terminus of the exodomain with a stop codon and flanking XbaI site (GTAGTCTAGATCATTGGCTACTTTCACC AGAG) (SEQ ID NO: 223)

In each case the PCR products were cloned into the IL3 signal-FLAG-pEFBOS vector as previously described (Lackmann, 1996, supra). DNA was electroporated into CHO cells (Lackmann, 1996, supra), and high producer clones were selected by "dot blot" screening of culture supernatants on PVDF membranes, and the expected size of the recombinant proteins confirmed by SDS-PAGE and Western blot analysis using M2 anti-FLAG mAb and rabbit anti-mouse alkaline phosphatase (AP)-tagged mAb for detection by enhanced chemiluminescence (ECL, Amersham).

Deletion mutants were purified on M2 anti-FLAG affinity columns and elute with FLAG peptide according to the manufacturers instructions. Homogeneous preparations (>95% a by SDS-PAGE and silver staining) were obtained by anion-exchange chromatography (Mono Q, 5×50 mm, Pharmacia, Uppsala, Sweden) and size exclusion chromatography (Superose 12, 10×300 mm, Pharmacia, Uppsala, Sweden). The identity and concentration of the purified HEK proteins in the final preparations were confirmed by N-terminal amino add sequence analysis and amino acid analysis and, where applicable, their native conformation confirmed on the BIAcore as previously described (Lackmann, 1995, supra).

3. Production of LERK-3 and LERK7 (AL-1) expression

The 5' LERK7 oligonucleotide (GTAGTCTAGACAGGACCCGGGCTCAAGGC) (SEQ ID NO: 24) was based on the N-terminal amino acid sequence (QDPGSKA) (SEQ ID NO: 25) of the mature protein, with a 5' tag sequence and XbaI site preceding the coding nucleotides. The PCR reaction was performed using an aliquot of a placental cDNA library (kindly provided by Dr Tracy Wilson, Walter & Eliza Hall Institute) and Taq EXTEND (Boehringer-Mannhelm). A 490 bp product was detected on a 1.4% TAE/agarose gel. This was excised and the DNA purified using Geneclean II (BIO101). The PCR product and the IL3 sig-FLAG-pEFBOS vector (Nicola Bt al., 1996) were digested with XbaI and the vector treated with calf intestinal alkaline phosphatase to prevent re-ligation. After ligation correctly oriented clones were detected and verified by automated DNA sequencing as already described.

4. Transfection of cells with LERK3 and LERK7 DNA

Purified LERK 7-pEFBOS DNA was transfected into CHO cells. Briefly, $2 \times 10^7$ cells were suspended in 500-μl of PBS and 10 μg of LERK-pEFBOS DNA and 1 μg of pSV2 neo DNA added. After mixing and transfer to a 0.4 cm electroporation cuvette (BloRad), the cells were electroporated at 270 V and 960 μF and the cells centrifuged through an FCS underlayer. Transfected clones were selected in medium containing 600 μg/ml of G418. Individual clones were isolated and samples (5 μl) of CHO cell supernatants from confluent cultures were dotted onto a nitrocellulose membrane, air-died and re-hydrated in blocking buffer (5% skim milk powder/0.1% Tween 20 in PBS) prior to incubation with M2 anti-FLAG antibody at 1:1000 dilution. After washing the blot was incubated with horse radish peroxidase-conjugated rabbit ant-mouse Ig antibody (1:1000, Dako) in blocking buffer and following further washes developed with the ECL detection system (Amersham). Positives clones, indicated by signals above background, were retested by SDS-PAGE (12%) and Western blots prepared and probed as described above to confirm the presence of FLAG-tagged proteins of the expected molecular size.

6. Production of FLAG-tagged LERK7/AL-1

LERK7/AL-1 containing an N-terminal FLAG peptide was purified from transfected CHO cell supernatants by affinity purification on anti-FLAG mAb-conjugated agarose according to the manufacturer's protocol (IBI Kodak, New Haven Conn.) followed by MonoQ (Pharmacia Biotech) ion exchange chromatography in 20 mM Triis. pH 8.5/0.02% Tween 20 at 1 ml/min using a linear, 40 min gradient from 0–600 mM NaCl and size exclusion-HPLC (Superose 12,10/30, Pharmacia Biotech) in 20 mM Tris. The homogeneity, concentration and identity of the purified protein were confirmed by reverse phase-HPLC. SDS-PAGE, amino acid analysis and N-terminal amino acid sequence analysis as described (Lackmann et at., 1996, supra; Simpson et al., 1986).

6. Synthesis of HEK-derived peptides

A peptide having an amino acid sequence corresponding to residues Glu 21 to Gly 61 of the sequence shown in FIG. 1 was assembled by solid-phase peptide synthesis according to standard protocols, purified by reverse phase-HPLC and its mass confirmed by mass spectrometry.

7. Analysis of the interaction between HEK constructs and LERK7

The binding of various HEK constructs and derived peptides was analysed on the BIAcore optical biosensor (Pharmacia Biosensor, Sweden) using purified soluble HEK (corresponding to the entire extracellular domain) or LERK 7-FLAG derivatised CM 5 sensor chips and the interaction kinetics determined. The immobilization of HEK onto the sensor chip surface was performed essentially as described by Lackmann et al, 1996. LERK7-FLAG (47 μg/ml in 20 mM sodium acetate, pH 4.5) was coupled at 5 μl/min onto N-hydroxysuccinimide (NHS, 0.05 M)/N-hydroxysuccinimide-N-ethyl-N'-(diethylaminopropyl) carbodiimide(EDC, 0.2 M) activated sensor chips (45 μl, 2 μl/min) to yield an increase in the response level of 2500–3000 response units (RU).

The interaction kinetics of LERK-binding to immobilised HEK was analysed from raw data of the BIAcore sensorgrams suitable for analysis using linear and non-linear kinetic models included in the BIAevaluation software (Biosensor, P., 1995, BIAtechnology Handbook, Pharamacia Blosensor AB, Uppsala, Sweden). All results recorded in this report were within the typical dynamic ranges of BIAcore measurements and the BIAevaluation software. Single component kinetics was derived from:

$$\text{dissociation: } R=R_0 \cdot e^{-k_d(t-t_0)} \quad \text{(equation 1)}$$

$$\text{dissociation: } R=R_0/k_{\ominus}(1-e^{-k_s(t-t_0)}) \quad \text{(equation 2)}$$

or $$R=R_{eq}(1-e^{-k_s(t-t_0)}); k_s=k_\zeta C+k_d \quad \text{(equation 3)}$$

where $R_0$ is the response time at time $t_0$, $R_{eq}$ the steady state response level (not necessarily reached in the sensorgram) and C the molar concentration of the analyte. The two component dissociation was derived from:

$$R=R_1 e^{(-k_{d1} \cdot (t-t_0))}+(R_0-R_1)e^{-k_{d2} \cdot (t-t_0)} \quad \text{(equation 4)}.$$

Apparent affinities of LERKs 3, 4, 5, 7 were also derived from equilibrium responses according to:

$$R_{eq}/C=K_A R_{max}-K_A R_{eq} \quad \text{(equation 5)}$$

where $R_{eq}$ and $R_{max}$ are the equilibrium and maximum response levels, respectively. In addition to the analysis of ligand binding to sensor chip-immobilised HEK, the interaction between LERK-3 and LERK-7 with HEK was studied in solution. A constant ligand concentration was incubated with increasing concentrations of the soluble receptor. The free ligand concentration ($F_{LERK}$), estimated from the BIAcore™ response of a known LERK sample was used to calculate the concentration of bound receptor ($[B_{Hek}]$) or ligand ($[B_{LERK}]$), and free HEK ($F_{Hek}$) using the initial receptor concentration ($T_{Hek}$) and assuming in this case a single site interaction: $[F_{Hek}]=[T_{Hek}]-[B_{Hek} \cdot B_{LERK}]$, where $[B_{Hek} \cdot B_{LERK}]=[B_{Hek}]=[B_{LERK}]$.

Thus the dissociation constant, $K_D$, was estimated from:

$$K_D = \frac{[F_{Hek}] \cdot [F_{LERK}]}{[B_{Hek} \cdot B_{LERK}]} = [F_{Hek}]\frac{[F_{LERK}]}{[B_{LERK}]} \quad \text{(equation 6)}$$

according to word et at., 1995, Biochemistry 34 2901–7 and Scatchard transformation yielded:

$$\frac{[B_{LERK}]}{[F_{LERK}]} = \frac{1}{K_D}[F_{Hek}]$$

The effect of HEK-derived peptides oh the interaction of HEK with LERK 7 was tested by incubation of a constant concentration of the ligand with increasing amounts of peptide prior to analysis on a HEK-derivatised sensor chip as previously described. The affinity surface was regenerated between subsequent injections of samples with a 35 μl-injection of 50 mM, 1,2-diethylamine/0.1% Triton X100, followed by two washes with-BIAcore running buffer (HEPES-buffered saline/0.005% Tween 20).

8. Fish care and embryo collection

Wild type zebrafish were obtained from St. Kilda Aquarium (Melbourne) and were kept essentially as described by Westerfield et al., 1995, The Zebrafish Book, 3rd ed., University of Oregon Press, Oregon. Embryos were obtained by natural spawning between a small number (4–10) of male and female fish. Embryos were removed from the spawning tanks within 20 minutes of fertilisation, cleaned in system water, and transferred to the injection apparatus.

9. mRNA synthesis

Constructs encoding HEK I–VII, HEK IV–VII and LERK7 were generated by PCR from the cDNA constructs described above. In each case the 5' oligonucleotide was based on the IL-3 signal sequence and the 3' oligonucleotides were as above except that Bgl II sites were used to clone the PCR products into the pSP64TK vector. mRNA from the HEK and LERK7 constructs and a control E-GFP CDNA construct were transcribed in vitro using the mMessage mMaker kit (Ambion, Tex.) and resuspended in water at a concentration of 0.1 mg/mL in small aliquot. Integrity of the RNA was checked by denaturing gel electrophoresis of the resulting products. Immediately prior to injection, aliquots of HEK I–VII, HEK IV–VII or LERK7 were thawed and mixed with water and E-GFP mRNA to a final concentration such that either 100 pg, 10 pg, or 1 pg of the mRNA, and 5 pg of the E-GFP mRNA were delivered to each embryo.

10. Microinjection

Approximately 600 pl of mRNA, dissolved in water at the desired concentrations, was injected into one-, two- or four-cell embryos under a Wild stereo microscope using Leitz micromanipulators (Leitz, Wetzlar, Germany) and compressed nitrogen. The needle was positioned under the blastoderm in the region of cytoplasmic streaming. Successful injection was judged in the first instance by a visible bolus of fluid in the embryo. Uptake and translation of mRNA by the embryo was measured by including 5 pg mRNA encoding E-GFP as a marker in each injection. Injection of over 100 pg E-GFP mRNA per embryo does not cause developmental defects. The translation of the injected HEK mRNA was measured at intervals during embryogenesis by Western blotting. Ten embryos per time point were lysed in embryo lysis buffer (25 mM Tri-HCl, pH 7.4, 0.5M NaCl, 1% Triton X-100), immunoprecipitated with anti-FLAG M2 mAb-conjugated agarose, subjected to SDS-PAGE, transferred to PVDF-Plue membranes and Western blotted with M2 mAb. Detection of antigen was visualised using ECL. Protein levels were quantitated by densitometric comparison with HEK-FLAG mass standards run in the same gel.

11. Analysis of developmental defects

The effects on embryonic growth of each of the injected mRNAs were measured in two ways. Firstly, embryos were allowed to grow for twelve to thirteen hours post-fertilisation (five to eight somite stage; Kimmel et al., 1995) their gross morphology was noted under a dissecting microscope, and the perturbation of early gene expression patterns was assayed by in situ hybridisation using digoxigenin-labeled RNA probes. Secondly, embryos were scored as defective if a typical pattern of gene expression was aberrant e.g. misshapen, missing or ectopic.

EXAMPLE 1

Genomic Structure of the Extracellular Region of the HEK Gene

A human genomic library was screened with the HEK cDNA probes described above, and positive clones were characterized by restriction mapping and Southern blotting using exon-specific oligonucleotides derived from the HEK cDNA sequence. Exons were identified by sequencing subcloned genomic fragments, or by directly sequencing the phage clones with HEK oligonucleotides. A clone containing exon II was not obtained, and its sequence was inferred from the 3' and 5' junctions of exon I and exon III respectively. Sequences for intro-exon splice junctions were matched using the "GTAG rule" (Mount, 1982), and the results, summarised in Table 1 and FIG. 2A show that the extracellular region consists of seven exons interrupted by six introns.

Exon boundaries were determined by sequencing non-overlapping λ FIX II clones, and are shown for the extracellular domains of the HEK gene. This sequence is the flanking region of the start methionine, as deduced from the published cDNA sequence (Wioks et al., 1992, supra).

The parallel isolation and analysis of clones from a mouse genomic library containing exons II and III of SEK I, exon III of BSK, and exon IV of ESK indicates that this arrangement is a general feature of genes encoding Eph family RTKs. The results are illustrated in FIG. 1, and together with reports on the structure of chicken CEK 5 gene (Connor & Pasquale, 1995, Oncogene 11 2429–2438) and splice variants of other Eph family RTKs (Saijadi et al., 1991, supra; Maisonplerre et al., 1993, Oncogen 8 3277–3288) suggest that axon structure is highly conserved within the Eph family.

Exon I contains all of the 5' untranslated sequence and the first 88 bp of the coding sequence which includes the signal peptide, and together with exon II encodes the first 31 residues of the mature protein starting at residue 21 of the sequence shown in FIG. 1 (Wicks et al., 1994, Genomics 19 38–41). Exon III contains 10 of the 20 conserved cysteine residues characteristic of the Eph family RTKs. Although previous reports have described this cysteine-rich domain of Eph family kinases as being immunoglobulin-like, we found no significant homology between exon III and any other protein domains in the database using the ALIGN sequence alignment program. It has been suggested that the carboxy terminus of exon III is similar to an EGF-like repeat as it contains the consensus sequence motif CnCxCxxGYnC (Table 2, Connor & Pasquale, 1995, supra). Although the genomic organization is not typical of a repeat (see below), we believe that exon III arose from a fusion or shuffling of exons which once encoded an EGF-like module.

Database analysis of the exon IV sequence showed matches with EGF repeat regions in other proteins. Moreover, the six conserved cysteine residues follow a CnCnCnCXCnC pattern, which is characteristic of an EGF-like repeat (Table 2) found within the EGF precursor gene (Bell et al., 1986, Nucleic Acids Res. 14 8427–8446). EGF-like repeats are usually encoded by a discrete axon, as noted in the genomic organization of EGF precursor protein, LDL receptor, and human factor IX (Anson et al., 1984, EMBO J. 3 1053–1060; Sudhof of al., 1985, Science 228 815–822; Bell et al., 1988, supra).

The exon-intron borders of the two fibronectin (FN) domains correlate exactly with the borders predicted by analysis of the amino acid sequence. The first fibronectin type III repeat (FN I) is encoded by a single exon, which also contains the remaining four conserved cysteine residues found within Eph family RTKs. Exon VI and exon VII encode the second fibronectin repeat (FN II). The genomic organization of the fibronectin type III repeats is typical of the type III homology units found within the fibronectin gene and other proteins containing fibronectin repeats (Oldberg and Ruoslahti, 1986, J. Biol. Chem. 261 2113–216: Giger et al., 1995, Eur. J. Biochem. 227 617–628). The fibronectin type III units are encoded by either a single exon or by two exons; however, the units which are spliced out in various protein isoforms are usually those encoded by a single exon (Oldberg & Ruoslahti, 1986, supra). This is also observed with transcripts of Eph family members which lack FN I (Maisonplerre et al., 1993, supra).

EXAMPLE 2

Assignment of the Disulphide Bonds in HEK

The structural importance of disulphide bonds for the architecture of a protein or protein domain is undisputed. Although the connectivities of 8 of the conserved cysteines in exons III and IV are inferred from the respective domain structures, as shown in Table 2, assignment of remaining disulphide bridges in exon III and an experimental confirmation of the predicted Cys—Cys bonding pattern were critical requirements for a reliable expression of conformationally stable receptor subdomains.

In a strategy adapted from Hodder et al., 1996, we analysed reduced and non-reduced tryptic maps of the minimally-glycosylated HEK by analytical RP-HPLC, to rapidly Identify disulphide-containing fragments as absorbance peaks unique to the RP-HPLC profile of the non-reduced tryptic digest. Automated N-terminal amino acid sequence analysis and mass-spectrometry of these peptides enabled identification of the disulphides within the native HEK receptor exodomain.

Assignment of the following peptides was confirmed:

$Cys_n$-$Cys_{189}$ (C1–C4)

$Cys_{257}$ or $_{259}$-$Cys_{270}$ (C8/9–C10)

$Cys_{305}$-$Cys_{322}$ (C15–C16)

$Cys_{352}$-$Cys_{365}$ (C17–C18).

EXAMPLE 3

Expression and Purification of HEK Subdomains

Figure 2B:
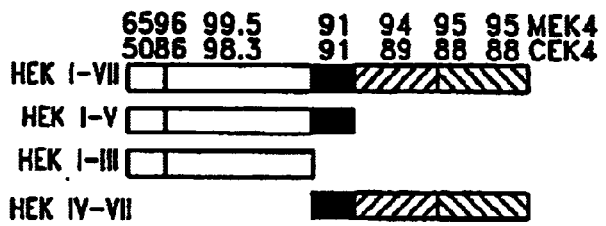
FIG. 2B. Exon structure corresponding to various soluble HEK (sHEK) constructs. The exons are indicated by differential shading from left to right as follows: exons I+II, exon III, exon IV, exon V, exons VI+VII. The isolation of exons belonging to HEK, SEK1, BSK and ESK genes is described herein. Exon VII from the MEK4 gene was reported in Saijadi et al. (1991) New Biologist 3 769–778.

A series of HEK cDNA constructs, as illustrated in FIG. 2B were transiently transfected into COS 7 cells, and the resulting culture supernatants were screened by immunodetection with anti-FLAG M2 mAb for the production of recombinant proteins. Constructs yielding proteins of the expected size in culture supernatants were stably transfected into CHO cells. Appreciable expression levels were found for HEK proteins, designated HEK I–VII (exons I–VII), HEK I–IV (exons I–IV), HEK I–III (exons I–III), HEK IV–VII (exons IV–VII), and HEK V–VII (exons V–VII). Western blot analysis of the expressed proteins revealed the expected apparent molecular sizes for HEK I–VII (68 kD). HEK I–IV (36 kD), HEK I–III (33 kD), HEK IV–VII (40 kD), and HEK V–VII (36 kD). Interestingly, no expression was observed for any of the protein constructs containing the exon III-encoded domain, but missing the first 31 amino acids of the mature HEK protein (encoded by exons I and II; amino acids 21–51 of the sequence shown in FIG. 1), suggesting impaired transcription, translation or stability of these constructs.

Purification of HEK I–VII, HEK I–IV, HEK I–III and HEK IV–VII by anti-FLAG mAb-affinity chromatography followed by anion exchange HPLC (HEK I–VII and HEK I–IV) or size exclusion-HPLC (HEK I–III and HEK IV–VII) yielded homogenous preparations, as shown in FIG. 2B, which were suitable for analysis of their interactions with LERK7 on the BIAcore.

EXAMPLE 4

Binding of Various LERK-Fc Fusion Proteins to Sensorchip-Immobilized HEK

Figure 2C:
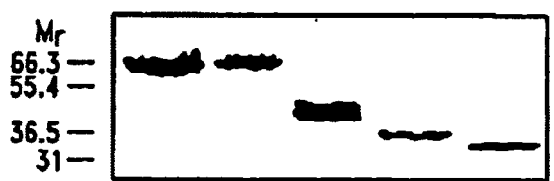
FIG. 2C: Expression of soluble HEK (sHEK) polypeptides encoded by the constructs shown in B. sHEK in lane 1 corresponds to the complete extracellular domain (exodomain) of HEK encoded by exons I–VII. Soluble HEK I–VII in lane 2 includes a FLAG tag, hence the slightly slower migration.
Figure 4:
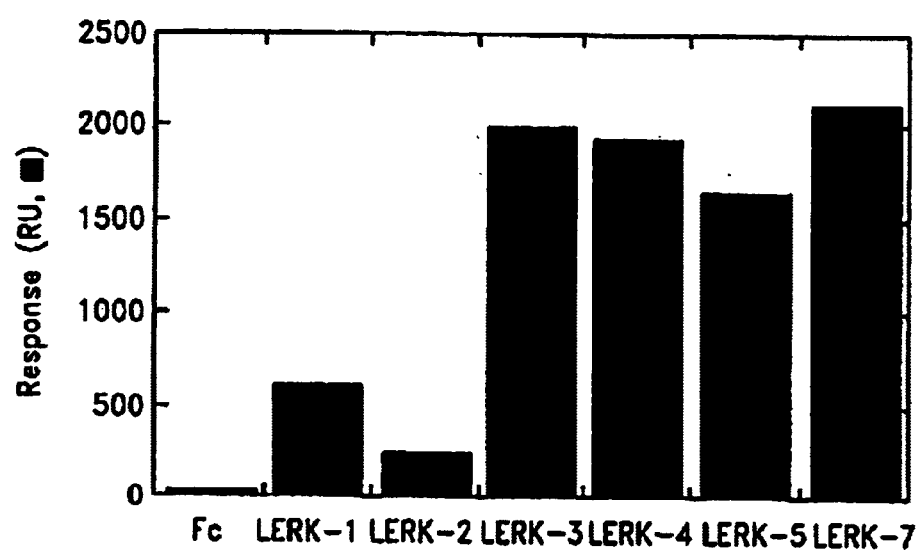
FIG. 4: Shows a comparison of the binding of LERK-Fc fusion proteins to sensor chip-immobilised HEK. Samples (50 μl) of purified fusion proteins comprising the human Fc domain and either LERK 1, 2, 3, 4, 5 and 7 at 10 μg/ml in BIAcore running buffer were applied onto an sHEK-derivatised sensor chip. The responses were recorded 20 s after completion of the injection phase and are shown as relative BIAcore response units, (RU) compared to the response of an equal amount of human Fc domain used as a control in this experiment.

Receptor-ligand interactions within the Eph family RTKs has mainly been studied by modified indirect Scatchard analysis of human IgG-Fc fusion proteins of ligands or receptors binding to receptor or ligand transfected cells, respectively (Beckmann et al., 1994, supra; Davis et al., 1994, supra; Ceretti et al., 1995, supra: Bennett et at., 1995). To evaluate if BIAcore analysis also detected the interaction of various LERKs with HEK, we compared the binding of bivalent, Fc-fusion proteins of LERK (LERKS 1 to 5) and LERK 7 (FIG. 2C) to sensor chip-immobilised HEK exodomain. Each ligand sample was injected at concentrations between 0.1–10 µg/ml (approximately 0.8 to 80 nM) across the sensor chip. A sample containing 10 µg/ml of the recombinant Human Fc fragment was used as a control. The relative binding response units (RU) of various samples at 10 µg/n are illustrated in FIG. 4, indicating comparable responses for LERKs 3, 4, 5 and 7 which were considerably greater than the responses of LERK 1 and LERK 2. Apparent dissociation constants derived from equilibrium responses (equation 4) at the four highest concentrations suggested a decreasing order of nanomolar affinities, as follows:

LERK 7>LERK 3>LERK 4>>LERK 5 (data not shown).

The interactions with LERKs 1 and 2 did not reach equilibrium responses in our experiments, and hence precluded estimation of dissociation constants. Only background binding was seen with the control recombinant Fc construct, alone.

EXAMPLE 5

Interaction Kinetics of LERK 3-FLAG and LERK 7-FLAG Binding to HEK

To evaluate the contribution of bivalency of Fc ligand constructs to the interaction kinetics, we performed binding experiments with monovalent forms of LERK 3 and LERK 7. Corresponding FLAG-tagged fusion proteins were expressed in CHO cells and purified to homogeneity from culture supernatants of selected clones by anti-FLAG mAb affinity chromatography and ion exchange HPLC. The identity of the recombinant ligand proteins was confirmed by N-terminal amino acid sequence analysis.

A qualitative comparison of the BIAcore data, illustrating binding of increasing amounts of LERK 3-FLAG, (FIG. 5A) and LERK 7-FLAG (FIG. 4B) to a HEK sensor chip, reveals marked differences in the kinetics of the two interactions. The LERK3/HEK interaction is characterized by extremely fast on and off rates, and comparable responses of LERK3 or LERK7 binding to HEK were found only at approximately 30-fold higher LERK3 concentrations in the applied sample.

Kinetic analysis of the association and dissociation phases using a single component model yielded apparent association and dissociation rate constants of $k_2=4.8\pm0.13\times10^5$ $M^{-1}s^{-1}$ and $k_d=6.1\pm0.8 \times10^{-5}s^{-1}$ for LERK7, $k_2=3.7\pm0.9\times$ $10^5$ M$^{-1}$s$^{-1}$ and k$_d$=0.26±0.06 s$^{-1}$ for LERK 3. Apparent dissociation constants K$_D$=1.2×10$^{-5}$ M for LERK 7-FLAG and K$_D$=5.9(±0.4)×10$^{-7}$ M for LERK 3-FLAG were estimated.

Analysis of the raw data revealed good fits to linear, "one-to-one" interactions, yielding Chi square values of 0.64±0.18 and 0.47±0.06 for the LERK 7 and LERK 3 reactions, respectively. The apparent equilibrium affinity constant for LERK 7 was substantiated by Scatchard analysis of the in-solution, interaction (Ward et at., 1995, supra), yielding an identical dissociation constant of K$_D$=1.2×10$^{-8}$ M. On the other hand, the affinity of the LERK3/FLAG Interaction was too low to obtain reliable data by "insolution" analysis.

Cross linking of LERK-FLAG with anti FLAG mAb alters interaction with HEK

We next addressed the possibility that the differences observed in the binding of either FLAG-tagged and Fc-tagged ligands to sensorchip-Immobilised HEK were due to increased avidity of the divalent Fc tagged ligands. To quantitatively examine this effect in situ, we assembled bivalent ligand/mAb complexes before or during BIAcore experiments by cross-linking FLAG-tagged LERK 7 (FIGS. 6A, 6B) and LERK-3 (FIGS. 6C, 6D) with the anti-FLAGm M2 mAb.

The interactions of preformed LERK-FLAG/M2 mAb complexes (FIGS. 6B, 6D, graph e) with a HEK-derivatised sensor chip resulted in 3- to 6-fold increased BIAcore responses and markedly reduced off-rates of the ligand/antibody complexes compared to the non-complexed LERK-FLAG proteins (FIGS. 6A, 6C, graph c), reflecting the increased size, and indicating an altered avidity, of the interacting complexes. To confirm this, we injected FLAG peptide, to compete with the LERK-FLAG proteins for anti-FLAG mAb binding sites, into the dissociation phase of LERK-FLAG/M2 mAb complex (FIG. BB, graph-f). A dramatically increased of off-rate in this experiment confirmed that the suggested increase in avidity was dependent upon anti-FLAG mAb-mediated cross linking of LERK-FLAG.

Figure 8:
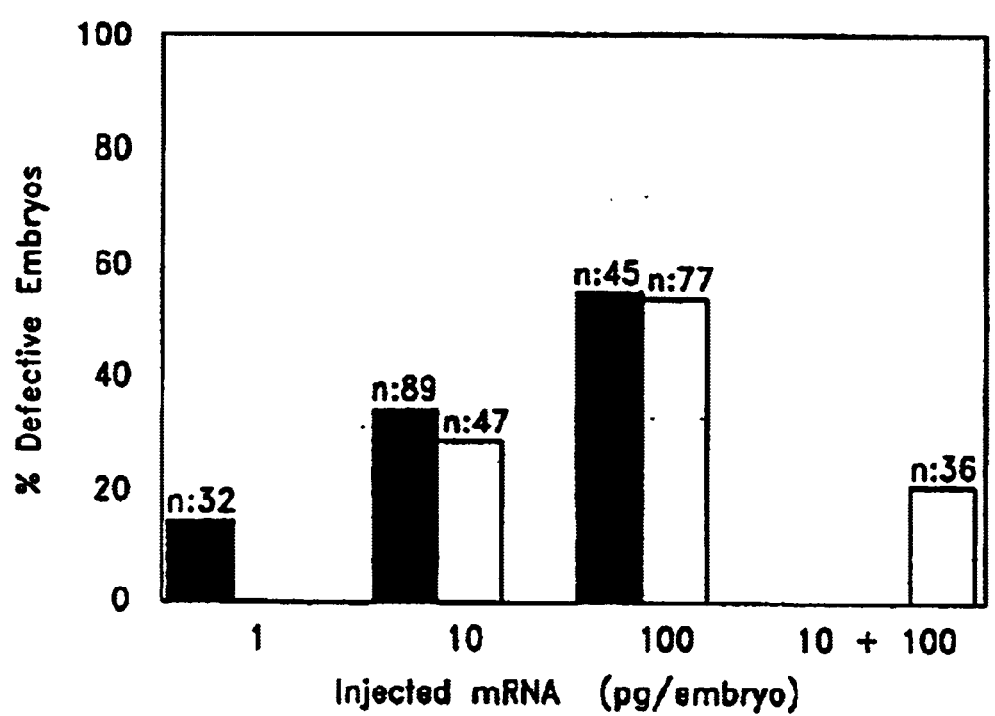
FIG. 8: Dose response and phenotypic rescue of soluble HEK and LERK7-induced developmental defects. Batches embryos, injected with indicated amounts of HEK mRNA (□), LERK7 mRNA (9) or a combination of 10pg HEK mRNA and 100 LERK7 mRNA (□) and a constant amount of E-GFP mRNA (5pg) were allowed to grow for 12–13 hpf before fixation and hybridisation with *pax-b*, *hix*-1, *krox*20 and *myoD* DIG-labeled riboprobes. Embryos were analysed under a dissecting microscope and scored for aberrant patterns of gene expression. Non-injected control embryos were scored after an identical developmental period and identical handling to the injected embryos to control for defects due to the genetic background of particular parents in our strain. None of these embryos showed any reproducible or significant defects.

Furthermore, injection of the anti-FLAG M2 mAb at the end of the first injection cycle resulted in a pronounced rise of the BIAcore signals, likely due to binding of newly-formed ligand/mAb complexes (FIGS. 6B, 6D, graph d). The increase of the responses above the levels observed with the monovalent ligands in the first part of the sensorgram, presumably reflects the increased size of the interacting ligand/mAb complexes. On the other hand, amplitude and slope of the response curve are also determined by the abundance and affinity of the ligand available for complex formation at the time of mAb injection. Since injection of equimolar amounts of LERK 3-Fc or LERK 7-Fc is expected to yield the same ligand concentrations at the end of the first injection cycles, differences in the amplitude of the response following mAb injection (compare graph d in FIGS. 6B, 6D) must portray primarily the different affinities of the LERK-FLAG/M2 mAb complexes. In support of this, the dissociation curves and the response levels of pre-formed (graph e) and in situ formed (graph d) ligand/mAb complexes at the end of the second injection cycle (after 1090 s) were found to be identical (FIG. 8D) or very similar (FIG. 6B).

Taken together, these strictly qualitative analyses demonstrate that anti-FLAG M2 mAb crosslinked LERK-FLAG dimers bind HEK with increased avidity due to decreased dissociation rates. The resulting response curves are qualitatively very similar to the sensorgrams of the corresponding LERK-Fc fusion proteins, suggesting that avidity plays a major role in the interaction kinetics of these ligand constructs.

EXAMPLE 6

Induction of HEK Phosphorylation in Ligand-Treated Cell Cultures

In addition to the kinetic analysis of the LERK-HEK interaction, we compared the ability of either LERK 3 or LERK 7 to mediate transphosphorylation of HEK in LK63 cells, which have been shown to express the receptor constitutively (Boyd et al. 1992, supra). LK63 cell cultures were incubated with buffer or solutions containing either LERK 3-FLAG, LERK 7-FLAG or pre-formed complexes of these ligands with anti-FLAG M2 mAb. In the latter samples the concentrations of LERK-FLAG proteins and M2 mAb were adjusted to provide divalent ligand constructs by occupancy of both binding domains of the mAb with ligand-FLAG. The HEK receptor was then immunoprecipitated from the cells and analysed by western blot analysis. Phosphotyrosine analysis showed no significant differences between control, LERK 3FLAG or LERK 7-FLAG treated samples. In contrast, incubation of cells with LERK 3-FLAG/M2 mAb complex induced a small but significant increase, and incubation with LERK 7-FLAG/M2 mAb complex gave a dramatic increase in phosphotyrosine content of HEK. Corresponding bands on the anti-HEK probed blots show no significant difference in total HEK protein between the experimental groups.

EXAMPLE 7

BIAcore Analysis Reveals the Exon III Encoded Cys-Rich Region of the HEK Exodomain as the LERK-7 Binding Domain The interactions between Eph family receptors and their ligands have commonly been analysed by an Indirect Scatchard analysis of divalent receptor-exodomain/IgG, Fc fusion proteins binding to ligand-expressing cells, revealing equilibrium dissociation constants in the low nanomolar range (Winslow, 1995, Neuron 14 973–981; Beckmann et al., 1994, supra; Davis et al., 199, supra; Gale et al., 1996, supra). In all these previous studies, the contribution of the avidity of the bivalent Fc-fusion proteins has not been appreciated. In contrast, we have found an estimated K$_D$ of 12 nM for the binding of LERK 7 to BIAcore sensor chip-immobilised monovalent HEK.

To evaluate the contribution of the various HEK subdomains to the receptor/ligand interaction, we followed a similar strategy and performed a kinetic BIAcore analysis on the binding of HEK I–VII, I–IV, I–III and HEK IV–VII to sensor chip-immobilised LERK 7. Deconvolution of the BIAcore raw data during the association and dissociation phases and Scatchard analysis of the equilibrium responses (Biosensor, 1995, supra) demonstrated monovalent, linear receptor/ligand interactions.

Figure 2D:
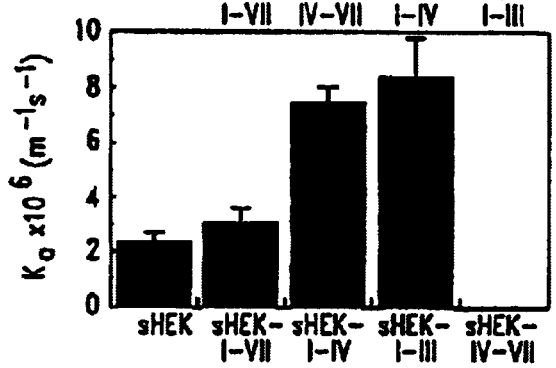
FIG. 2D: sHEK proteins at increasing concentrations (15.6–500 nM) were injected onto LERK 7-derivatised sensor chips and the association rate constants, (M) derived from BIAcore raw data using the BIA evaluation software as described in *Materials and Methods*.
Figure 2E:
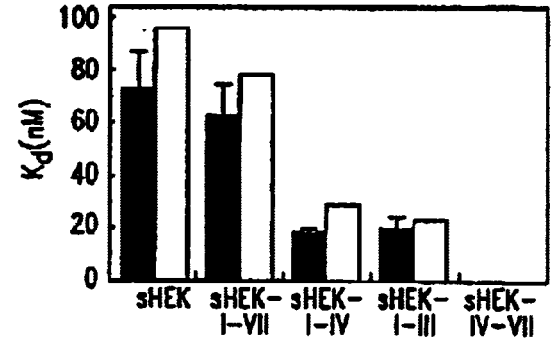
FIG. 2E; The kinetic rate constants were then used to estimate apparent dissociation constants according to $K_D$=kd/ka. The mean and standard deviation from estimates at five different concentrations are shown (dark shading). In addition, equilibrium responses were used to estimate the apparent equilibrium dissociation constants (light shading).

Substantially lower dissociation constants (i.e. higher affinities) of 18–29 nM, due to increased association rate constants (FIG. 2D), were observed for the interaction between LERK 7 and the HEK subdomain constructs HEK I–IV and HEK I–III (FIG. 2E). On the other hand, the very similar apparent dissociation constants of 72±15 and 62±12 nM for sHEK and FLAG-tagged HEK I respectively, and insignificantly higher equilibrium dissociation constants as shown in FIG. 2E, suggested that an N-terminal addition of the FLAG epitope had no effect on the interaction between HEK and its ligand. Higher diffusion rates of the significantly smaller HEK subdomain constructs I–IV and I–III, and possibly an improved accessibility of the ligand binding interface, are the most-likely reasons for the apparently increased affinity of these constructs observed in the BIAcore experiments.

Figure 2F:
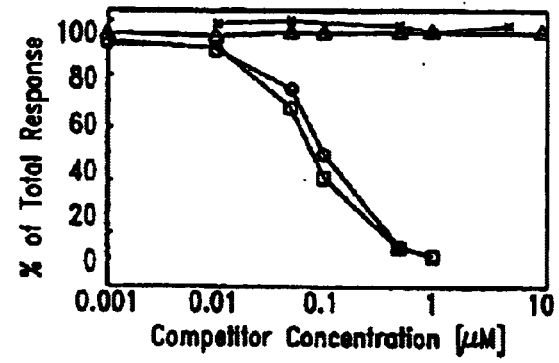
FIG. 2F: Samples containing 40 nM LERK 7 and 1 nM—10 μM synthetic peptide encoded by exons I and II of the HEK gene (Δ), 10 nM—1 μM HEK I–VII (o), 10 nM—1 μM HEK IV–VII (x) or 1 nM—1 μM HEK I-III (□) were injected onto an sHEK-derivatised sensor chip. The residual responses are illustrated as percentage of the total response in the absence of competitor.

Importantly, no binding of HEK IV–VII to immobilised LERK 7 was observed at any of the concentrations tested (16–500 nM), thus identifying the ligand binding site as lying within the N-terminal portion encoded by exons I–III of HEK. To evaluate the contribution of the most N-terminal 31 amino acid residues of the mature HEK protein (amino acids 21–51 of FIG. 1), encoded by HEK exons I and II, we performed in-solution competition studies with a synthetic peptide, corresponding to this part of the HEK exodomain. The results, illustrated in FIG. 2F, suggest that the presence of the 31-residue N-terminal peptide at concentrations up to 10 μM had no effect on the receptor/ligand interaction, whereas addition of HEK I–II or HEK I–VII resulted in a dos-dependent reduction of the BIAcore response. Taken together, these results unambiguously demonstrate that the cysteine-rich domain encoded by HEK exon III contains a crucial part of the ligand binding domain.

EXAMPLE 8

The Effect of Ectopic HEK Expression in the Developing Zebrafish

Analysis of Eph family RTKs and their ligands has centered largely on their role in axon guidance (reviewed in Maller et al., 1996, supra; Friedman & O'Leary, 1996, supra; Tessier-Lavigne, 1995, supra), a process that occurs relatively late in embryogenesis. However, Eph family RTK are expressed at much earlier stages in embryogenesis (Cheng & Flanagan. 1994, supra; Henkemeyer, M., 1994, supra; Xu et al., 1994, supra; Gilardi-Hebenstreit, 1992, Oncogene 7 2499–2506; Nieto et al., 1992, supra; Scales et al., 1995, Oncogene 11 1745–1752; Lickliter et al., 1996, Proc. Natl. Acad. Sci. USA 93 145–150), and little is known about what role they might play at this stage. To address this role we have used the zebrafish, a model which has been previously shown to be tractable to analysis of early embryonic events (Xu et al., 1995. Development 121 4005–4016; Xu of et al., 1996). These studies were remarkable because they demonstrated that ectopic expression of a mouse or Xenopus homologue of the zebrafish rtk1 gene could be used to perturb development. Moreover, the effects were specific to the targeted gene in that defects were confined to regions of the zebrafish embryo that expressed endogenous rtk1.

The putative zebrafish HEK homologue, rtk2, is expressed during gastrulation from 80 to 90% epiboly in the dorsal axis and in a ring around the yolk plug. As epiboly completes, higher expression levels are seen in the anterior neuraxis and in lateral cells of the neural plate aligned approximately with the mes-met boundary (Xu et al., 1994, supra). This localisation is similar to the patterns of the MEK 4 transcript in the mouse embryo, which are seen at day 8.5 (10 somites) and show high levels of expression at day 9.5 In the mid and hindbrain and within the paraxial mesoderm of the somites (Cheng & Flanagan, 1994, supra).

Figure 7:
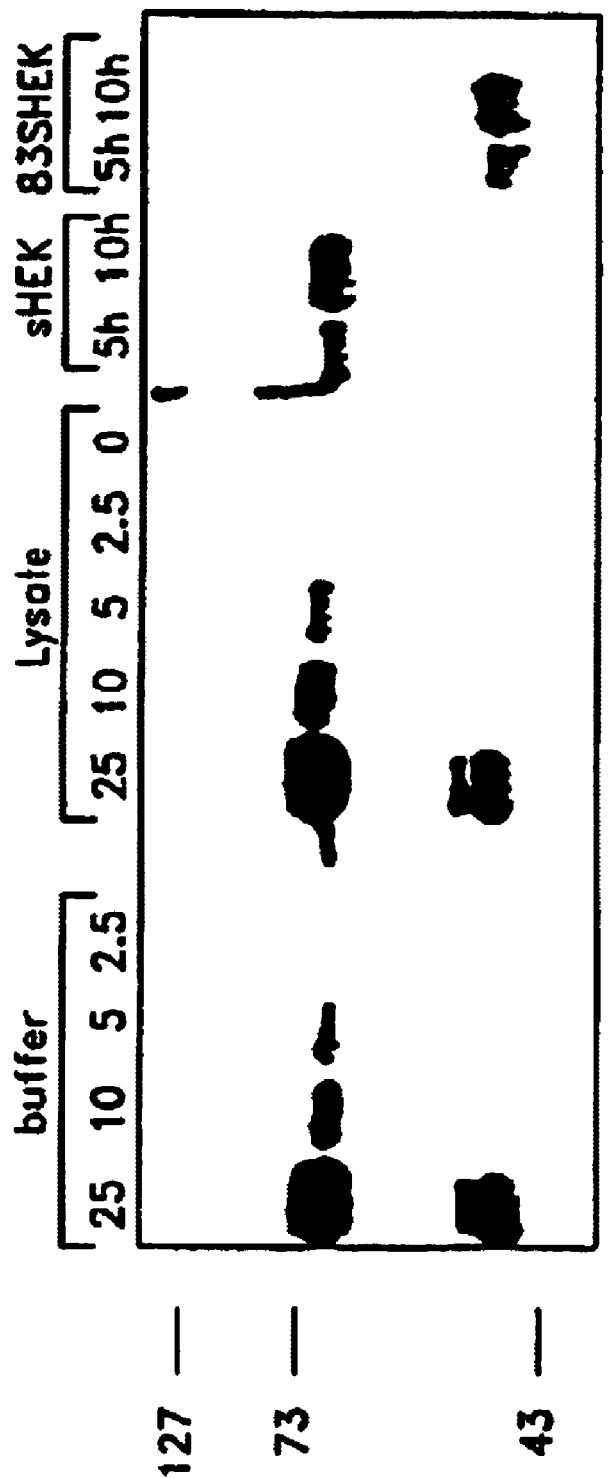
FIG. 7 Detection of expressed HEK I–VII and HEK IV–VII (far right lanes) in zebrafish embryos by Western blot and BIAcore analysis. Samples of lysis buffer or zebrafish lysates (10 embryos/0.1 ml) containing 25, 20, 5, 2.5 ng of HEK I–VII and HEK IV–VII were immunoprecipitated with anti-FLAG M2 mAb-agarose and analysed by Western blot. Zebrafish embryos injected with HEK I–VII mRNA or HEK IV–VII mRNA were lysed after 5 h or 10 h and analysed in parallel lanes of the gel. Specific detection of FLAG epitope-containing HEK proteins corresponding to the expected molecular weight in embryos at 5 and 10 hpf demonstrates that the recombinant fusion proteins were present in embryos throughout the period of development analysed here. Parallel BIAcore analysis of whole embryo lysates with sensorchips derivatised with native conformation-specific anti-HEK mAb (Boyd et al., 199, supra; Leokmann et al., 1996) detects the intact HEK exodomain at an apparent concentration of 120 to 240 ng per embryo (5 to 10 hpf, respectively, data not shown).

The present inventors reasoned that ectopic HEK exodomain expression may cause defects in brain development and somite organisation. Also, a high-affinity, 1:1 interaction between the HEK exodomain and monovalent LERK7 has been characterised and the need for ligand crosslinking (FIG. 7) or cell association (Wilson et al., 1995) for RTK activation suggests that both, receptor exodomain and soluble ligand could serve as antagonists of signalling via the zebrafish HEK homolog.

The present inventors also reasoned that ectopic HEK exodomain expression may cause defects in the brain formation and somite of the zebrafish embryo. Therefore, the effect of a soluble, secreted form of the HEK RTK and of the ligand LERK 7 was tested on zebra-fish development. This was compared this with a mutant HEK lacking the exon III-encoded LERK-7 binding domain identified previously. A soluble form of the mouse HEK homolog, MEK 4, has been isolated from an embryonic cDNA library (Saijadi et ea., 1991, supra), suggesting that the early mouse embryo is exposed to this form of the HEK protein. mRNA encoding HEK I–VII or encoding LERK7-FLAG (LERK 7 mRNA), was introduced into zebrafish embryos at the single, two and four cell stages by microinjection into the yolk cell immediately under the blastoderm. mRNA introduced at this stage becomes ubiquitously distributed throughout the embryo (FIG. 10D). We detected the presence of a FLAG epitope-containing protein corresponding to the expected molecular weight in embryos from 5 hpf until 10 hpf (FIG. 10A), at an apparent concentration of 0.5–1 ng/embryo, demonstrating that the protein was present in embryos throughout the period of development analysed here.

EXAMPLE 9

Injection of HEK Exodomain mRNA Causes Patterning Defects in Early Embryogenesis Animals injected with HEK mRNA or LERK7 mRNA developed a consistent syndrome in a concentration dependent manner. Inspection of the animals between 11 and 15 hpf revealed defects involving reduced dorsal axis height from the yolk cell, disorganised anterior neuraxis, and disorganised somite boundaries (FIGS. 8A–F).

In severe cases of the syndrome at 12 hpf (FIGS. 8B and 8E) there was little morphological differentiation visible along the anterior-posterior aspect of the dorsal axis. Axial tissue was flattened over the yolk cell and somites were elongated laterally, much as in the trilobite mutant (Hammershmodt et al., 1996; Kane et al., 1996; Solnica-Krezel et al., 1996; Stemple et al., 1996), and disorganised, often out of register across the dorsal midline. The anterior neuraxis was also disorganised so that optic vesicle formation was retarded, and the characteristic mid- and hindbrain seamentation visible at 13 hpf was reduced or absent (FIGS. 8B, 8E, 8C, 8F).

In less severely affected embryos, the defects were predominantly confined to the anterior portion of the dorsal axis.

EXAMPLE 10

Analysis of Marker Gene Expression

In order to better understand the nature of the defect and to allow a more objective quantitation of the proportion of embryos displaying defeots, embryos injected with mRNA encoding soluble HEK and soluble LERK7 at three different mRNA concentrations (100 pg, 10 pg and 1 pg per embryo) were fixed between 12 and 13 hpf, and marker gene expression was analysed. Animals were considered defective if in situ hybridisation with probes to hix-1 (Fjose, 1994), paxb (Kraus, 1991), krox20 (Oxtoby & Jowett, 1993), and myoD (Weinberg et al., 1994) revealed abnormal patterns consistent with ectopic gene expression. A dose-dependent effect of HEK mRNA was seen across two orders of magnitude mRNA concentration (FIG. 11). The nature of these defects is consistent with the gross morphological observations (FIGS. 9A, 9B) presented above. The most profound defect compared with normal, uninjected embryos, is the failure of the mid, and hind brain and trunk paraxial mesoderm to fuse across the dorsal midline (FIGS. 9C–F). The forebrain region was intact, as indicated by a single axially-located stripe of hix-1 expression in the ventral forebrain. Cells expressing paxb and krox20 of the mid-and hindbrain respectively are arrayed in lateral stripes at some distance from the dorsal midline. Non-injected control embryos, or embryos injected with with E-GFP mRNA alone, do not show this defect (FIGS. 9A, 9B). Thus a large gap separating left and right halves of the embryo is present from the posterior limit of the forebrain until the anterior level of the somites. This analysis suggests that there has been a failure of the cells of the mid-and hind-brain to converge to the dorsal axis correctly. Disorganised myoD expression conforms (FIGS. 9D, 9F) the observation in living embryos that many somites are out of register across the midline. This defect could result from a failure of lateral cells to converge to the midline, a conclusion consistent with the laterally-extended somitic segmentation seen in live embryos. However, a disruption of anterior-posterior patterning processes cannot be ruled out. A coherence of phenotypes in response to exogenous expression of either receptor exodomain or soluble ligand indicate speciffic rather than promiscuous activation of the endogenous HEK homologue by a putative zebrafish homologue of LERK 7.

We verified this notion by markedly reducing the number of defective embryos by co-injecting HEK mRNA together with LERK 7 mRNA (not shown). Importantly, our experiments confirm a strict conservation of structural and functional specificity of Eph family RTK In vertebrate development.

EXAMPLE 11

Deletion of the Ligand Binding Domain of HEK Rescues Embryonic Development

The assignment in vitro of the domain in HEK that is required for high affinity binding to LERK 7 by methods as described in Example 4, was tested in vivo by introduction of mutated versions of soluble HEK into zebrafish embryos. We have shown that the extodomain of HEK requires the presence of the sequence encoded by exon III for high affinity binding to LERK 7. This assignment suggests that removal of exon III from the HEK mRNA injected into zebrafish embryos should abrogate developmental defects due to the interaction of HEK with ligands through the ligand-binding domain. Therefore, HEK IV–VII mRNA, was injected into zebrafish embryos at the same range of concentrations at which the full-length HEK mRNA had produced defective development. The resulting embryos were assayed and scored for disrupted marker-gene expression patterns as described above.

No significant developmental defects were detected in embryos injected with either 10 pg or 1 pg HEK IV–VII mRNA per embryo, either by gross morphological criteria (FIG. 10C), or by analysis of marker gene expression (FIG. 10G). Ubiquitous E-GFP expression (FIG. 10D) and detection of approximately 0.4–1.0 ng HEK protein per embryo by Western blotting (FIG. 10A) during development indicate that the protein was widely and highly expressed. Thus the failure of cells to converge to the dorsal midline in embryos injected with HEK mRNA is a function of the exon III-encoded ligand binding domain, and is probably due to interaction of this domain with one or more LERK-like ligands, present in the embryo. Interestingly, at high concentrations (100 pg per embryo) of injected HEK IV–VII mRNA, there was no difference in the proportion of defective embryos when compared to full length HEK mRNA-injected embryos. This indicates that at high concentrations of HEK exodomain, the developmental perturbation becomes effectively ligand independent and indicates a distinct receptor dimerisation interface.

DISCUSSION

Figures 5A, 5B:
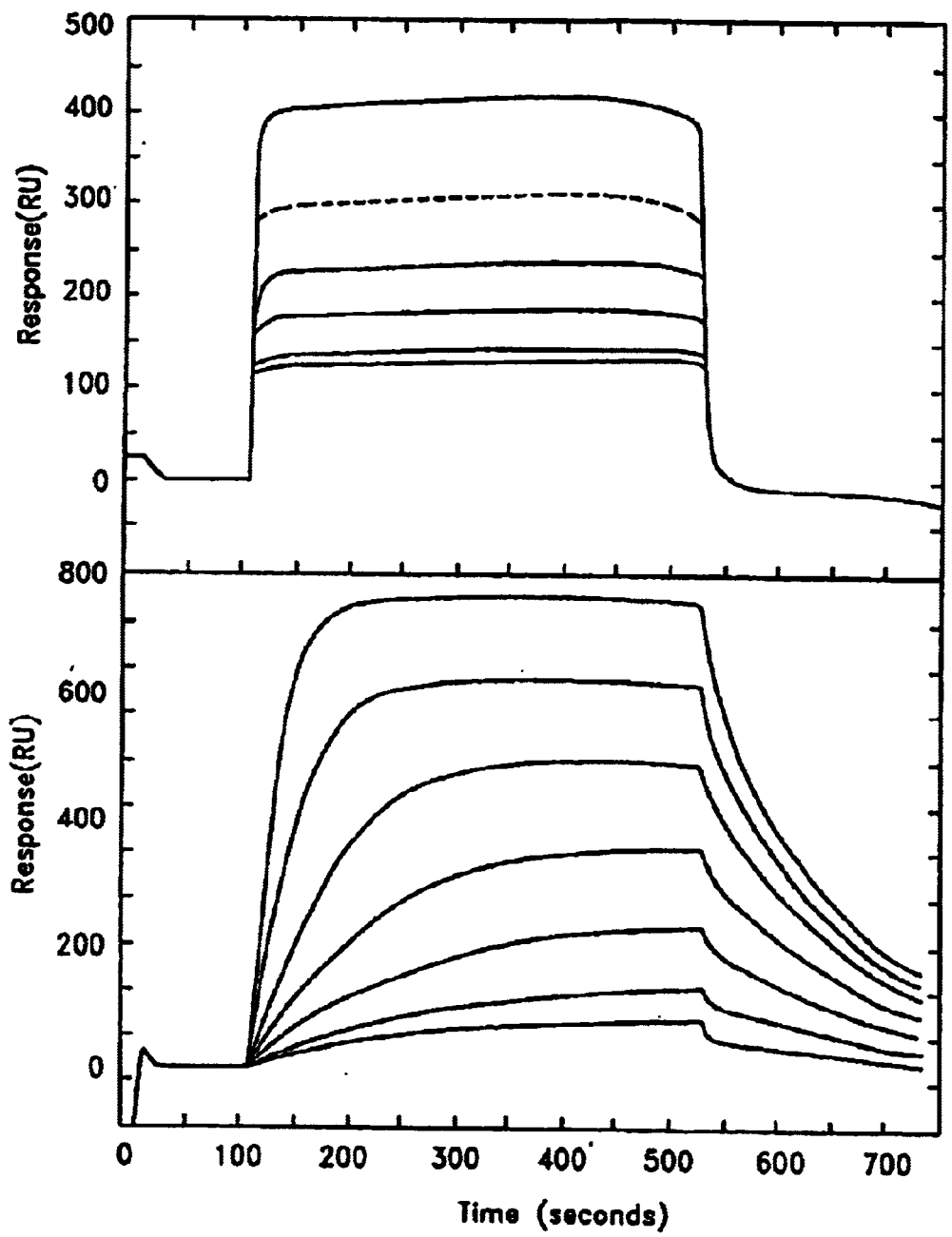
FIG. 5: Binding curves for the interaction of monovalent LERK-FLAG fusion proteins with immobilised sHEK. Homogeneous preparations of CHO cell-derived LERK 3-FLAG (panel A) or LERK 7-FLAG (panel B) at increasing concentrations (8.22, 16.44, 32.88, 65.75, 131.5, 263, 526 nM) of LERK3-FLAG, and (1.25, 2.5, 5, 10, 20, 40, 80 nM) LERK7-FLAG were injected across an sHEK-derivatised sensor surface. BIAcore data for the association and dissociation phases were used to estimate corresponding kinetic rate constants on the basis of a one-to-one interaction model. (panel C). Free sHEK was estimated in samples with increasing sHEK and a constant LERK 7-FLAG concentration at equilibrium and used to calculate the equilibrium dissociation constant $K_D$ by Scatchard analysis.
Figure 5C:
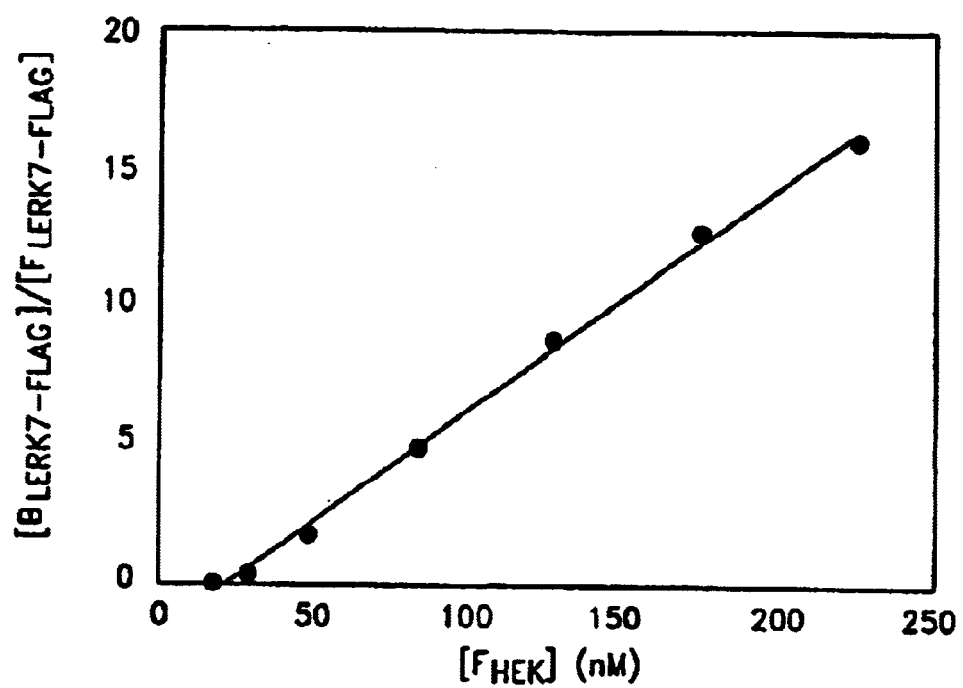

Most of the studies of Eph family RTKs and their ligands carried out to date have been performed with divalent Fc fusion constructs of either ligand or receptor. The present inventors compared the binding of different LERK-Fc fusion proteins to HEK-derivatised sensor chips, and confirmed the suggested cross-reactivity of all the tested LERK-Fc constructs with HEK (FIG. 5). In accord with these reports, the interaction between HEK and Fc constructs of LERK 1 and 2 was distinctively weaker than binding of LERKs 3 and 4, which in our experiments yielded similar BIAcore responses to LERK 7. On the other hand, while the previously published affinities of LERKs 1, 2 and LERK 5-Fc for HEK are very similar (18, 43, and 23 nM, respectively; Beckmann et al., 1994, supra; Cerretti et 9L, 1995, supra), we could estimate apparent dissociation constants only from equilibrium responses of LERKs 3,4,5 and LERK7-Fc ($K_D$s Of 5, 6, 24 and 3 nM, receptively), whereas binding of LERKs 1 and 2 was too weak for a kinetic analysis. In addition, biphasic binding was reported previously only for the interaction between HEK-Fc with LERK 2, where a low affinity constant of 430 nM was found (Beckmann et al., 1994, supra). Our comparative analysis of the association and dissociation phases of two candidate HEK ligands, LERK 3 (Kozlosky et al., 1996, supra) and LERK 7 (Lackmann et al., 1996, supra) indicated a concentration-dependent increase of the apparent dissociation rate constants (not shown), and an increasingly poor fit to the assumed one-component dissociation model.

A significant deviation of the divalent LERK-Fc kinetics from linear, single component interactions, suggesting a high-affinity interaction at low concentrations and a low-affinity interaction at high ligand concentrations confirms earlier studies by Hogg et al., 1987, and Posner et al., 1991, which demonstrate that kinetic models based on a one-to-one stoichiometry do not adequately describe the dissociation of bivalent solutes from surface-bound receptors.

The use of different approaches for the kinetic analysis of HEK/LERK-Fc interactions could explain the differences between the published data and the findings herein described. A direct evaluation of kinetic data from BIAcore progress curves is likely to be more sensitive to changes in kinetic rate constants than indirect Scatchard analysis, which relies on the use of labeled mouse anti-human IgG antibodies to detect receptor-Fc fusion proteins bound to ligand-transfected cells (see, for example, Davis et al, 1994, supra; Beckman et al., 1994, supra). Competitive binding experiments of the LERK-Fc/HEK interaction in solution (FIG. 7) which are not affected by immobilisation artefacts and/or rebinding of dissociating ligand (Ward et al., 1995, supra; Chatellier et al., 1998) but rely on an "indirect" estimation of bound ligand or receptor (see Methods), gave no direct indication of biphasic kinetics from the slope of the Scatchard plots but yielded negative [$B_{LERK}/F_{LERK}$] values at low HEK concentrations, thus indicating artefactually high responses in these samples. The interaction of bivalent LERK 7-Fc containing only a single bound HEK, via the remaining free LERK 7 moiety to the HEK sensor surface, is a likely explanation for this artefact and confirms the concentration-dependent bivalency of the LERK-Fe/HEK interaction.

The comparative evaluation of all our binding data suggests that the bivalent, high-affinity interaction of two covalently linked binding domains of the LERK-Fc fusion protein with two adjacent, sensorchip-immobilised receptor molecules will compete at saturating ligand-Fc concentrations with a low-affinity, monovalent interaction of a single binding domain with a single receptor molecule. Similar effects have been described for the analysis of mAb/antigen interactions (see, for example, Chatellier et al., 1995, supra) and for the interaction of dimerio IL-6 with the sensorchip-immobilised IL-6 receptor-exodomain (Ward et al., 1996, supra).

In other studies Eph receptor/LERK Interactions, the effect of solute bivalency has not been addressed. The necessity of ligand clustering for efficient receptor activation (Winslow et al., 1995, supra; Davis et el., 1994, supra; Cerretti et al., 1995, supra) seemed to warrant the use of bivalent receptor ligand constructs. Such constructs were also used most recently in whole embryo in situ staining to confirm kinetic experiments performed with the some receptor-Fc constructs (Gals et al., 1996, supra). On the other hand, it remains to be demonstrated that the interaction between membrane-bound ligands or receptor, and Fc-tethered bivalent receptors or ligands is a suitable system to study kinetics of physiological interactions of membrane-bound ligands and receptors (Pandey et al., 1995, supra). Our experiments indicate that the artificial bivalency of the ligand constructs obscures an unambiguous analysis of the reaction kinetics. In agreement with a report on the kinetics of the cell adhesion molecule CD2 and its GPI-anchored ligand, CD48 (van der Merwe at al., 1993) we find that very low affinity, due to fast ligand dissociation, is apparently increased by high avidity-binding of multimeric ligand aggregates.

By analysing the binding of monovalent LERKs to HEK, either in solution (not shown) or using the (sensor) surface immobilised receptor (FIGS. 5 and 6), we were able to characterise the receptor/ligand interaction in detail. In situ-crosslinking of the monovalent ligands with a mAb during BIAcore experiments (FIG. 6) and prior to SE-HPLC analysis of LERK/HEK complexes (not shown) demonstrated qualitatively the effect of avidity on the interaction and confirmed the apparent higher affinities of bivalent ligand constructs. Differences in the dissociation phases of specific LERK interactions were concealed by the higher avidity of divalent binding components (FIG. 6) but have a major impact on the affinities of the monovalent ligands (FIGS. 5 and 6). Due to an extremely fast off-rate, the interaction of monovalent LERK3-FLAG with the immobilised receptor is very weak (FIG. 5B), an observation confirmed in solution which indicated an unstable, transient LERK3-FLAG/HEK complex. By contrast, binding of LERK 7-FLAG to HEK was characterised by a 40-times lower off rate and resulted in a stable receptor/ligand complex (not shown) which was confirmed by kinetic analysis of HEK binding to sensor chip-immobilised LERK 7, yielding an apparent $K_D$ of 7.2 $\times 10^{-8}$ M. The dissociation rate of the LERK7-FLAG/HEK reaction was low enough to allow purification of the ligand/receptor complex from solution and to facilitate its characterisation by equilibrium sedimentation analysis.

The demonstration of a 1:1 stoichiometry confirms our results from BIA core and SE-HPLC experiments indicating that HEK has a single binding site for LERK7, and explaining the necessity of ligand crosslinking for receptor activation and transphosphorylation demonstrated in this study (FIG. 7) and reported by others (Davis et al., 1994, supra; Brambilla et al. 1996, supra).

Our results clearly identify LERK7 as the best candidate for a physiological HEK ligand. Despite very similar apparent affinity constants for the LERK3 and LERK7 Fc fusion proteins, the interaction between their monovalent analogues and HEK differs substantially by a markedly higher dissociation rate of LERK3"-FLAG protein. Cross-linking of the dissociating ligands with anti-FLAG-mAb decreases the dissociation rates and results in similar interaction kinetics for both ligands. Our results could suggest that the reported interactions between some of the LERKs and HEK are influenced by the choice of the ligand construct. Extrapolating our observations to the in vivo situation, it seems likely that LERK 3 functions as an effective ligand only at very high receptor and ligand densities on opposing cell membranes, whereas a stable LERK7/HEK complex persists at much lower receptor and ligand numbers.

SUMMARY

Identification of the Ligand Binding Domain Mechanism of Perturbation of Vertebrate Embryogenesis with Soluble HEK Exodomain and Soluble LERK Specialised roles during vertebrate development have been described for a limited number of Eph-family RTK and their corresponding ligands (Cheng et al., 1995, supra, Drescher et al., 1995, supra, Nakamoto et al., 1996, supra) and together with the high interspecies conservation of primary protein structures argues for conserved and specific functions of defined Eph receptor/ligand interactions. A comparison between the amino arid sequences for the extracellular domains of HEK and is murine (MEK4) and chicken (CEK4) homologues (96 and 91% overall identity, respectively) demonstrates highest identityin the exon III encoded domain (99.6% and 99.3%, respectively, FIG. 2A) and suggests a high evolutionary constraint on the structure of this domain. By analysing the interactions of the receptor exodomain and derived subdomains (FIG. 2) with its high-affinity ligand in vitro by BIAcore analysis and in vivo by expression in zebrafish, we were able to confirm this notion. BIAcore experiments summarised in FIG. 2 demonstrate that the exon III-encoded domain is neccessary for high-affinity ligand binding.

Whereas expression of the HEK exodomain or of soluble LERK 7 during zebrafish embryogenesis results in dose-dependent disruption of midline development, expression of the truncated receptor lacking the ligand binding domain gives rise to unaffected embryos, emphasising the role of a HEK/LERK7 derived signal during vertebrate development. A partial rescue of the wildtype phenotype by co-injection of receptor exodomain and soluble LERK 7 mRNA suppports the specificity of the observed HEK-LERK 7 interaction.

We assume that the expressed soluble HEK protein at in a dominant negative manner in the embryo. Previous studies in cell culture and in embryos have demonstrated that signalling through RTKs is inhibited by co-expression of kinase-deleted or truncated forms of the receptor (Honegger et al., 1990; Frattali et al., 1992a, be Spirtz et al., 1992; Reith at ea., 1993; Peters et al., 1994, Dumont et al., 1994). This inhibition is thought to proceed via the formation of a dimeric complex on the surface of cells, in which an endogenous full-length length receptor pairs with the exogenous truncated receptor, resulting in a complex that cannot autophosphorylate, and hence is inactive in signaling (reviewed in Van der Geer et al., 1994, supra).

The formation of these complexes can be either ligaind dependent (Ueno et at, 1993) or independent (Frattali et al., 1992a,b, supra; LeviToledano, 1994). Expression of a kinase domain-deficient Eph family RTK has been used previously to disrupt the signaling of rtk1/sek1 in zebrafish embryos (Xu et at., 1996, supra).

We interpret the results described here using a model in which the secreted HEK extracellular domain binds soluble LERK7 or binds to an endogenous receptor-ligand multimer and render this complex inactive. These soluble forms can also bind ligand (receptor) independently of the endogenous receptor (ligand), as demonstrated by our results in vitro thereby tiitrating the ligand (receptor) from the system. Both molecular mechanisms have the same effect: a decrease in the number of active cell surface receptor-ligand signaling complexes. Recent results indicate that transmembrane Eph receptor ligands may have the capacity to transduce a signal into the cells on which they are expressed (Holland et al., 1998, Bruckner et al., 1997). However, as LERK 7 is GPI-linked to the cell surface, ligation by HEK is not expected to generate a signal in this manner.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

TABLE 1

| EXON | SPLICE ACCEPTOR | | | | SPLICE DONOR | | | |
|---|---|---|---|---|---|---|---|---|
| I* (88 bp) | ccagcaac | M ATG | D GAT | C TGT | S TCC | N AAT | E GAA G | gtaagcca |
| II# (65 bp) | | V TC | N AAT | L CTA | S TCA | H CAT | G GGG | |
| III (661 bp) | ttcttcag | W TGG | E GAA | E GAG | M ATG | C TGC | Q CAA C | gtaagagc |
| IV (156 bp) | gtttgtag | A CT | C TGT | R CGA | A GCT | C TGT | T ACC C | gtgagtag |
| V (336 bp) | ctttgcag | R GA | P CCT | P CCA | N AAT | Q CAG | A GCT | gtgagtac |
| VI (126 bp) | ctttacag | A CT | P CCA | S TCA | Y TAT | E GAA | K AAG | gtggggaa |
| VII (163 bp) | cctcaaag | Q CAG | E GAA | Q CAA | S AGT | P CCA | D GAC T | gtatgtat |

LEGENDS

Table 1

A λ clone for this exon was not isolated; the exon boundaries are deduced from the boundaries of the adjacent exons.

TABLE 2

| EGF-like repeats | | |
|---|---|---|
| C - (12) - C S C N A G Y - (6) - C | Hek | |
| C - (12) - C L C N A G H - (6) - C | SEK1 | |
| C - (12) - C H C E P G Y - (8) - C | EPH | Exon III |
| C - (12) - C M C R P G Y - (8) - C | CEK5 | |
| C - (12) - C T C K A G Y - (7) - C | ELK | |
| C - (13) - C A K C - (13) - C R C E N N Y - (11) - C | Hek | |
| C - (13) - C A K C - (13) - C T C D R G F - (11) - C | SEK1 | |
| C - (13) - C L T C - (13) - C T C E S G H - (11) - C | EPH | Exon IV |
| C - (13) - C V H C - (13) - C V C R N G Y - (11) - C | CEK5 | |
| C - (13) - C S H C - (13) - C T C R T G Y - (11) - C | ELK | |
| C - (7) - C S Q L C - (9) - C D C F P G Y - (8) - C | PREPRO-EGF | |
| C - (6) - C E H I C - (8) - C S C R E G F - (8) - C | PREPRO-EGF | |
| C - (6) - C S H V C - (8) - C L C P D G F - (7) - C | LDL Receptor | |
| C - (6) - C D Q F C - (8) - C S C A R G Y - (8) - C | Factor X | |
| C - (6) - C E Q F C - (9) - C S C T E G Y - (8) - C | Factor IX | |
| C - (6) - C A H Y C - (8) - C S C A P G Y - (8) - C | Protein C | |
| C (n) C (n) C (n) C x C xx G Y/F (n) C | CONSENSUS | |

What is claimed is:

1. An isolated polypeptide which binds a ligand selected from the group consisting of LERK3, LERK4, LERK5 and LERK7, wherein said isolated polypeptide consists of the amino acid sequence set forth in SEQ ID NO:4.

2. The isolated polypeptide of claim 1, wherein said polypeptide has at least one pair of disulfide cysteine residues selected from the group consisting of:

(i) $Cys_{71}$-$Cys_{189}$; and (ii) $Cys_{259}$-$Cys_{270}$, wherein said cysteine residues are identified in SEQ ID NO:4.

3. An isolated polypeptide which binds a LERK, said polypeptide consisting of the amino acid sequence of SEQ ID NO:4.

4. The polypeptide of claim 3, wherein the LERK is LERK7.

5. The isolated polypeptide of claim 1 which is a recombinant polypeptide produced by a host cell.

6. A method of identifying a molecule which binds the polypeptide of claim 1, which method includes the steps of:

(i) combining a sample suspected of containing said molecule with the polypeptide of claim 1; and (ii) determining if said molecule is present in said sample by measuring the binding of the molecule to said polypeptide; wherein binding identifies said molecule.

7. A method of identifying a molecule which competes with binding of a ligand to the polypeptide of claim 1, which method includes the steps of:

(i) combining a sample suspected of containing said molecule, a ligand and at the polypeptide of claim 1; and (ii) determining if the molecule is present in the sample by measuring the competitive binding of the molecule and the ligand with said polypeptide; wherein a molecule that competes with ligand for binding to said polypeptide identifies said molecule.

* * * * *

UNITED STATES PATENT AND TRADEMARK OFFICE
CERTIFICATE OF CORRECTION

PATENT NO. : 7,037,662 B1
APPLICATION NO. : 09/104340
DATED : May 2, 2006
INVENTOR(S) : Boyd et al.

It is certified that error appears in the above-identified patent and that said Letters Patent is hereby corrected as shown below:

At the First page, column 2 (Abstract), line 4, please delete "gone" and insert --gene-- therefor.

At column 1, line 24, please delete "Neumbiol" and insert --Neurobiol-- therefor.

At column 1, line 26, please delete "(TOF-β)" and insert --(TGF-β)-- therefor.

At column 1, line 41 (approx.), please delete "simulation" and insert --stimulation-- therefor.

At column 1, line 54, please delete "Bemstein" and insert --Bernstein-- therefor.

At column 1, line 57, please delete "348:" and insert --348;-- therefor.

At column 1, line 58, please delete "A." and insert --A.,-- therefor.

At column 2, line 1, please delete "Chang" and insert --Cheng-- therefor.

At column 2, line 2, please delete "et al." and insert --et al.,-- therefor.

At column 2, line 8, please delete "(Hiral" and insert --(Hirai-- therefor.

At column 2, line 10, please delete "7:" and insert --7;-- therefor.

At column 2, line 14 (approx.), please delete "et at.," and insert --et al.,-- therefor.

At column 2, line 34 (approx.), please delete "at al.," and insert --et al.,-- therefor.

At column 2, line 36 (approx.), please delete "(LERKS:" and insert --(LERKS;-- therefor.

At column 2, line 36 (approx.), please delete "et at.," and insert --et al.,-- therefor.

At column 2, line 43, please delete "et al. 1994:" and insert --et al., 1994;-- therefor.

At column 2, line 45 (approx.), please delete "Brambilia" and insert --Brambilla-- therefor.

At column 2, line 55, please delete "ill" and insert --III-- therefor.

At column 2, line 56, please delete "et at.," and insert --et al.,-- therefor.

At column 2, line 59, please delete "crossreactivity" and insert --cross-reactivity-- therefor.

At column 2, line 64, please delete "et al." and insert --et al.,-- therefor.

Signed and Sealed this

Thirtieth Day of November, 2010

David J. Kappos
*Director of the United States Patent and Trademark Office*

CERTIFICATE OF CORRECTION (continued)
U.S. Pat. No. 7,037,662 B1

At column 2, line 65, please delete "et oh," and insert --et al.,-- therefor.

At column 2, line 66, please delete "St al.," and insert --et al.,-- therefor.

At column 3, line 14, please delete "et at.," and insert --et al.,-- therefor.

At column 3, line 18-19, please delete "retinoteotal" and insert --retinotectal-- therefor.

At column 3, line 20, please delete "et at.," and insert --et al.,-- therefor.

At column 3, line 21, please delete "370," and insert --370;-- therefor.

At column 3, line 22, please delete "et at.," and insert --et al.,-- therefor.

At column 3, line 23 (approx.), please delete "OBJET" and insert --OBJECT-- therefor.

At column 3, line 32 (approx.), please delete "high affinity" and insert --high-affinity-- therefor.

At column 3, line 45, please delete "Is" and insert --is-- therefor.

At column 3, line 64, please delete "axon I, axon" and insert --exon I, exon-- therefor.

At column 4, line 4, please delete "FIG" and insert --FIG.-- therefor.

At column 4, line 14, please delete "adds" and insert --acids-- therefor.

At column 4, line 17, after "NO:4)" delete ",".

At column 4, line 26, please delete "axon" and insert --exon-- therefor.

At column 4, line 50, please delete "se" and insert --as-- therefor.

At column 5, line 42, please delete "described," and insert --described-- therefor.

At column 5, line 49, please delete "20'" and insert --20°-- therefor.

At column 5, line 50, please delete "25'" and insert --25°-- therefor.

At column 5, line 51, please delete "10' to 15'" and insert --10° to 15°-- therefor.

At column 5, line 53, please delete "Is" and insert --is-- therefor.

At column 5, line 64, after "length" insert --.--.

At column 6, line 7 (approx.), please delete "60000" and insert --6000-- therefor.

At column 6, line 30, please delete "et al" and insert --et al.-- therefor.

At column 6, line 31, please delete "CLONING," and insert --CLONING.-- therefor.

At column 7, line 12 (approx.), please delete "add" and insert --acid-- therefor.

At column 7, line 49, please delete "calls" and insert --cells-- therefor.

At column 7, line 49, please delete "coils" and insert --cells-- therefor.

At column 8, line 11 (approx.), please delete "es" and insert --as-- therefor.

At column 8, line 16, please delete "end" and insert --and-- therefor.

At column 8, line 33 (approx.), please delete "subsequences" and insert --sub-sequences-- therefor.

At column 8, line 43-44, please delete "Collgan" and insert --Coligan-- therefor.

CERTIFICATE OF CORRECTION (continued)
U.S. Pat. No. 7,037,662 B1

At column 9, line 65, please delete "defect," and insert --defects,-- therefor.

At column 10, line 8, please delete "form" and insert --from-- therefor.

At column 10, line 30, please delete "according," and insert --according-- therefor.

At column 10, line 48 (approx.), please delete "NOS" and insert --NOS:-- therefor.

At column 10, line 49 (approx.), please delete "NOS" and insert --NOS:-- therefor.

At column 10, line 50 (approx.), please delete "NOS" and insert --NOS:-- therefor.

At column 10, line 50 (approx.), after "amino" please insert --acid--.

At column 10, line 51 (approx.), please delete "NO" and insert --NO:-- therefor.

At column 10, line 57 (approx.), please delete "2B." and insert --2B:-- therefor.

At column 10, line 64, please delete "Saijadi" and insert --Sajjadi-- therefor.

At column 11, line 9 (approx.), please delete "2E;" and insert --2E:-- therefor.

At column 11, line 27 (approx.), Delete "hydrophoblo" and insert --hydrophobic-- therefor.

At column 11, line 34 (approx.), Delete "tall" and insert --tail-- therefor.

At column 12, line 5, Delete "(1)" and insert --(I)-- therefor.

At column 12, line 8, Delete "7" and insert --7:-- therefor.

At column 12, line 23, Delete "199," and insert --1992,-- therefor.

At column 12, line 24, Delete "Leokmann" and insert --Lackmann-- therefor.

At column 12, line 28 (approx.), After "Batches" insert --of--.

At column 12, line 46 (approx.), Delete "Hek" and insert --HEK-- therefor.

At column 12, line 56, Delete "end" and insert --and-- therefor.

At column 12, line 61, Delete "blosensor" and insert --biosensor-- therefor.

At column 13, line 16, Delete "et at.," and insert --et al.,-- therefor.

At column 13, line 30, Delete "libary" and insert --library-- therefor.

At column 13, line 41, Delete "end" and insert --and-- therefor.

At column 13, line 44, Delete "C(bases" and insert --C (bases-- therefor.

At column 13, line 48, Delete "GTAGTCTAGACAAGCTTGTCGACCAGGTT" and insert --GTAGTCTAGACAAGCTTGTCGACCAGGTTT-- therefor.

At column 13, line 55, Delete "(Saijadi" and insert --(Sajjadi-- therefor.

At column 13, line 59, After "and" insert --λ--.

At column 13, line 60, Delete "Elize" and insert --Eliza-- therefor.

At column 13, line 64, Delete "In" and insert --in-- therefor.

At column 14, line 2, Delete "88°" and insert --68°-- therefor.

CERTIFICATE OF CORRECTION (continued)
U.S. Pat. No. 7,037,662 B1

At column 14, line 12, Delete "Biosysterris," and insert --Biosystems,-- therefor.

At column 14, line 20, Delete "17)," and insert --17)-- therefor.

At column 14, line 21, Delete "11)." and insert --18).-- therefor.

At column 14, line 28, Delete "Aced." and insert --Acad.-- therefor.

At column 14, line 31, Delete "N terminal" and insert --N-terminal-- therefor.

At column 14, line 41, Delete "IV-VI," and insert --IV-VII,-- therefor.

At column 14, line 47, Delete "223)" and insert --23).-- therefor.

At column 14, line 62, After "(>95%" delete "a".

At column 15, line 1, Delete "add" and insert --acid-- therefor.

At column 15, line 4, Delete "1995," and insert --1996,-- therefor.

At column 15, line 5, After "expression" insert --constructs--.

At column 15, line 7, Delete "(GTAGTCTAGACAGGACCCGGGCTCAAGGC)" and insert --(GTAGTCTAGACAGGACCCGGGCTCCAAGGC)-- therefor.

At column 15, line 14, Delete "Mannhelm)." and insert --Mannheim).-- therefor.

At column 15, line 17, Delete "Bt" and insert --et-- therefor.

At column 15, line 28 (approx.), Delete "(BloRad)," and insert --(BioRad),-- therefor.

At column 15, line 38 (approx.), Delete "ant-mouse" and insert --anti-mouse-- therefor.

At column 15, line 46, Delete "6." and insert --5.-- therefor.

At column 15, line 52 (approx.), Delete "Triis." and insert --Tris,-- therefor.

At column 15, line 54-55 (approx.), Delete "12,10/30," and insert --12, 10/30,-- therefor.

At column 15, line 56 (approx.), Delete "protein" and insert --proteins-- therefor.

At column 15, line 57 (approx.), Delete "HPLC." and insert --HPLC,-- therefor.

At column 15, line 59 (approx.), Delete "et at.," and insert --et al.,-- therefor.

At column 15, line 64, Delete "61" and insert --51-- therefor.

At column 16, line 10, Delete "et al," and insert --et al.,-- therefor.

At column 16, line 13-14, Delete ") carbodiimide" and insert --)-carbodiimide-- therefor.

At column 16, line 21, Delete "Pharamacia" and insert --Pharmacia-- therefor.

At column 16, line 22, Delete "Blosensor" and insert --Biosensor-- therefor.

At column 16, line 66 (approx.), Delete "word et at.," and insert --Ward et al.,-- therefor.

At column 17, line 5 (approx.), Delete "oh" and insert --on-- therefor.

At column 17, line 30 (approx.), Delete "CDNA" and insert --cDNA-- therefor.

At column 17, line 32 (approx.), Delete "aliquot." and insert --aliquots.-- therefor.

CERTIFICATE OF CORRECTION (continued)　　　　　　　　　　Page 5 of 8
U.S. Pat. No. 7,037,662 B1

At column 17, line 57, Delete "Plue" and insert --Plus-- therefor.

At column 18, line 19 (approx.), Delete "intro-exon" and insert --intron-exon-- therefor.

At column 18, line 29, Delete "(Wioks" and insert --(Wicks-- therefor.

At column 18, line 36 (approx.), Delete "(Saijadi" and insert --(Sajjadi -- therefor.

At column 18, line 37 (approx.), Delete "Maisonplerre" and insert --Maisonpierre-- therefor.

At column 18, line 37 (approx.), Delete "Oncogen" and insert --Oncogene-- therefor.

At column 18, line 38 (approx.), Delete "axon" and insert --exon-- therefor.

At column 18, line 63, Delete "axon," and insert --exon,-- therefor.

At column 18, line 66, Delete "of al.," and insert --et al.,-- therefor.

At column 18, line 67, Delete "1988," and insert --1986,-- therefor.

At column 19, line 10 (approx.), Delete "216:" and insert --216;-- therefor.

At column 19, line 17 (approx.), Delete "(Maisonplerre" and insert --(Maisonpierre-- therefor.

At column 19, line 33 (approx.), Delete "Identify" and insert --identify-- therefor.

At column 19, line 40 (approx.), Delete "$Cys_\eta$" and insert --$Cys_{71}$-- therefor.

At column 19, line 59 (approx.), Delete "kD)." and insert --kD),-- therefor.

At column 20, line 18, Delete "supra:" and insert --supra;-- therefor.

At column 20, line 18, Delete "et at.," and insert --et al.,-- therefor.

At column 20, line 27 (approx.), Delete "µg/n" and insert --µg/ml-- therefor.

At column 20, line 66, Delete "$k_2$" and insert --$k_a$-- therefor.

At column 20, line 67, Delete "$k_2$" and insert --$k_a$-- therefor.

At column 21. line 1, Delete "Apparant" and insert --Apparent-- therefor.

At column 21, line 9 (approx.), Delete "et at," and insert --et al.,-- therefor.

At column 21, line 11 (approx.), Delete "Interaction" and insert --interaction--.

At column 21, line 16 (approx.), Delete "Immobilised" and insert --immobilised-- therefor.

At column 21, line 31, Delete "BB," and insert --6B,-- therefor.

At column 21, line 53, Delete "8D)" and insert --6D)-- therefor.

At column 21, line 56, Delete "crosslinked" and insert --cross-linked-- therefor.

At column 22, line 3, Delete "et al." and insert --et al.,-- therefor.

At column 22, line 12 (approx.), Delete "3FLAG" and insert --3-FLAG-- therefor.

At column 22, line 26 (approx.), Delete "Indirect" and insert --indirect-- therefor.

At column 22, line 31 (approx.), Delete "199," and insert --1994,-- therefor.

At column 23, line 6, Delete "I–II" and insert --I–III-- therefor.

CERTIFICATE OF CORRECTION (continued)
U.S. Pat. No. 7,037,662 B1

At column 23, line 7, Delete "dos-dependent" and insert --dose-dependent-- therefor.

At column 23, line 21, Delete "Flanagan." and insert --Flanagan,-- therefor.

At column 23, line 28 (approx.), Delete "1995." and insert --1995,-- therefor.

At column 23, line 28 (approx.), After "Xu" delete "of".

At column 23, line 44, Delete "In" and insert --in-- therefor.

At column 23, line 50 (approx.), Delete "(FIG. 7)" and insert --(as hereinbefore described)-- therefor.

At column 23, line 62-63, Delete "(Saijadi et ea.," and insert --(Sajjadi et al.,-- therefor.

At column 24, line 3, Delete "(FIG. 10D)." and insert --.-- therefor.

At column 24, line 5, Delete "(FIG. 10A)," and insert --(FIG. 7),-- therefor.

At column 24, line 19, Delete "diorganised" and insert --disorganised-- therefor.

At column 24, line 19, Delete "(FIGS. 8A-F)." and insert --.-- therefor.

At column 24, line 20-21, After "12 hpf" delete "(FIGS. 8B and 8E)".

At column 24, line 29 (approx.), Delete "seamentation" and insert --segmentation-- therefor.

At column 24, line 29-30 (approx.), Delete "(FIGS. 8B, 8E, 8C, 8F)." and insert --.-- therefor.

At column 24, line 40 (approx.), Delete "defeots," and insert --defects,-- therefor.

At column 24, line 46 (approx.), Delete "(Kraus," and insert --(Krauss,-- therefor.

At column 24, line 50, Delete "(FIG. 11)." and insert --(FIG. 8).-- therefor.

At column 24, line 52, Delete "FIGS. 9A, 9B) presented above." and insert --.-- therefor.

At column 24, line 54 (approx.), Delete "(FIGS. 9C-F)." and insert --.-- therefor.

At column 24, line 60 (approx.), After "injected with" delete "with".

At column 24, line 61 (approx.), Delete "(FIGS. 9A, 9B)." and insert --.-- therefor.

At column 24, line 66-67, delete "conforms (FIGS. 9D, 9F)" and insert --confirms-- therefor.

At column 25, line 8, Delete "speciffic" and insert --specific-- therefor.

At column 25, line 14, Delete "In" and insert --in-- therefor.

At column 25, line 22 (approx.), Delete "high affinity" and insert --high-affinity-- therefor.

At column 25, line 25 (approx.), Delete "extodomain" and insert --exodomain-- therefor.

At column 25, line 26-27 (approx.), Delete "high affinity" and insert --high-affinity-- therefor.

At column 25, line 40, Delete "(FIG. 10C)," and insert --,-- therefor.

At column 25 line 40-41, Delete "(FIG. 10G)." and insert --.-- therefor.

At column 25, line 41, After "expression" delete "(FIG. 10D)".

At column 25, line 43, Delete "(FIG. 10A)" and insert --(FIG. 7)-- therefor.

At column 25, line 48 (approx.), Delete "ligands," and insert --ligands-- therefor.

CERTIFICATE OF CORRECTION (continued)

At column 25, line 65, Delete "LERK" and insert --LERKs-- therefor.

At column 26, line 4, Delete "9L," and insert --al.,-- therefor.

At column 26, line 7, Delete "receptively)," and insert --respectively),-- therefor.

At column 26, line 13 (approx.), Delete "1996," and insert --1995,-- therefor.

At column 26, line 33 (approx.), Delete "et al," and insert --et al.,-- therefor.

At column 26, line 35 (approx.), After solution delete "(FIG. 7)".

At column 26, line 38 (approx.), Delete "1998)" and insert --1996)-- therefor.

At column 26, line 47, Delete "LERK-Fe/HEK" and insert --LERK-Fc/HEK-- therefor.

At column 26, line 57 (approx.), Delete "dimerio" and insert --dimeric-- therefor.

At column 26, line 60, Delete "Interactions," and insert --interactions,-- therefor.

At column 26, line 63, Delete "et el.," and insert --et al.,-- therefor.

At column 26, line 65, Delete "receptor ligand" and insert --receptor-ligand-- therefor.

At column 26, line 67, Delete "some" and insert --same-- therefor.

At column 27, line 1, Delete "(Gals" and insert --(Gale-- therefor.

At column 27, line 10 (approx.), Delete "at al.," and insert --et al.,-- therefor.

At column 27, line 40 (approx.), Delete "experiments" and insert --experiments,-- therefor.

At column 27, line 44, Before "and" delete "(FIG.7)".

At column 27, line 45, Delete "al. 1996," and insert --al., 1995,-- therefor.

At column 27, line 51, Delete "LERK3″" and insert --LERK3-- therefor.

At column 27, line 65, After "LERK" insert --7-- therefor.

At column 28, line 6, Delete "arid" and insert --acid-- therefor.

At column 28, line 7, Delete "is" and insert --its-- therefor.

At column 28, line 9, Delete "identityin" and insert --identity in-- therefor.

At column 28, line 10, Delete "(99.6%" and insert --(99.5%-- therefor.

At column 28, line 10, Delete "respectively," and insert --respectively;-- therefor.

At column 28, line 17, Delete "neccessary" and insert --necessary-- therefor.

At column 28, line 26, Delete "suppports" and insert --supports-- therefor.

At column 28, line 28, Delete "at" and insert --acts-- therefor.

At column 28, line 31 (approx.), Delete "signalling" and insert --signaling-- therefor.

At column 28, line 33 (approx.), Delete "be Spirtz" and insert --b, Spritz-- therefor.

At column 28, line 34 (approx.), Delete "at ea.," and insert --et al.,-- therefor.

At column 28, line 41 (approx.), Delete "ligaind" and insert --ligand-- therefor.

CERTIFICATE OF CORRECTION (continued)
U.S. Pat. No. 7,037,662 B1

At column 28, line 42, Delete "et at," and insert --et al.,-- therefor.

At column 28, line 46, Delete "et at.," and insert --et al.,-- therefor.

At column 28, line 53 (approx.), Delete "tiitrating" and insert --titrating-- therefor.

At column 28, line 57, Delete "receptor ligands" and insert --receptor-ligands-- therefor.

At column 28, line 59, Delete "1998," and insert --1996,-- therefor.

SEQUENCE LISTING

<160> NUMBER OF SEQ ID NOS: 25

<210> SEQ ID NO 1
<211> LENGTH: 220
<212> TYPE: PRT
<213> ORGANISM: Homo sapiens
<220> FEATURE:
<221> NAME/KEY: DOMAIN
<222> LOCATION: (1)..(220)
<223> OTHER INFORMATION: Encoded by Exon III of HEK gene

<400> SEQUENCE: 1

Trp Glu Glu Ile Ser Gly Val Asp Glu His Tyr Thr Pro Ile Arg Thr
 1               5                  10                  15

Tyr Gln Val Cys Asn Val Met Asp His Ser Gln Asn Asn Trp Leu Arg
             20                  25                  30

Thr Asn Trp Val Pro Arg Asn Ser Ala Gln Lys Ile Tyr Val Glu Leu
         35                  40                  45

Lys Phe Thr Leu Arg Asp Cys Asn Ser Ile Pro Leu Val Leu Gly Thr
     50                  55                  60

Cys Lys Glu Thr Phe Asn Leu Tyr Tyr Met Glu Ser Asp Asp Asp His
 65                  70                  75                  80

Gly Val Lys Phe Arg Glu His Gln Phe Thr Lys Ile Asp Thr Ile Ala
                 85                  90                  95

Ala Asp Glu Ser Phe Thr Gln Met Asp Leu Gly Asp Arg Ile Leu Lys
            100                 105                 110

Leu Asn Thr Glu Ile Arg Glu Val Gly Pro Val Asn Lys Lys Gly Phe
        115                 120                 125

Tyr Leu Ala Phe Gln Asp Val Gly Ala Cys Val Ala Leu Val Ser Val
    130                 135                 140

Arg Val Tyr Phe Lys Lys Cys Pro Phe Thr Val Lys Asn Leu Ala Met
145                 150                 155                 160

Phe Pro Asp Thr Val Pro Met Asp Ser Gln Ser Leu Val Glu Val Arg
                165                 170                 175

Gly Ser Cys Val Asn Asn Ser Lys Glu Glu Asp Pro Pro Arg Met Tyr
            180                 185                 190

Cys Ser Thr Glu Gly Glu Trp Leu Val Pro Ile Gly Lys Cys Ser Cys
        195                 200                 205

Asn Ala Gly Tyr Glu Glu Arg Gly Phe Met Cys Gln
    210                 215                 220

<210> SEQ ID NO 2
<211> LENGTH: 22
<212> TYPE: PRT
<213> ORGANISM: Homo sapiens
<220> FEATURE:
<221> NAME/KEY: DOMAIN
<222> LOCATION: (1)..(22)
<223> OTHER INFORMATION: Encoded by Exon II of  HEK gene

<400> SEQUENCE: 2

Val Asn Leu Leu Asp Ser Lys Thr Ile Gln Gly Glu Leu Gly Trp Ile
 1               5                  10                  15

Ser Tyr Pro Ser His Gly
             20

<210> SEQ ID NO 3
<211> LENGTH: 29

```
<212> TYPE: PRT
<213> ORGANISM: Homo sapiens
<220> FEATURE:
<221> NAME/KEY: DOMAIN
<222> LOCATION: (1)..(29)
<223> OTHER INFORMATION: Encoded by Exon I of HEK gene

<400> SEQUENCE: 3

Met Asp Cys Gln Leu Ser Ile Leu Leu Leu Ser Cys Ser Val Leu
 1               5                  10                  15

Asp Ser Phe Gly Glu Leu Ile Pro Gln Pro Ser Asn Glu
            20                  25

<210> SEQ ID NO 4
<211> LENGTH: 271
<212> TYPE: PRT
<213> ORGANISM: Homo sapiens

<400> SEQUENCE: 4

Met Asp Cys Gln Leu Ser Ile Leu Leu Leu Ser Cys Ser Val Leu
 1               5                  10                  15

Asp Ser Phe Gly Glu Leu Ile Pro Gln Pro Ser Asn Glu Val Asn Leu
            20                  25                  30

Leu Asp Ser Lys Thr Ile Gln Gly Glu Leu Gly Trp Ile Ser Tyr Pro
        35                  40                  45

Ser His Gly Trp Glu Glu Ile Ser Gly Val Asp Glu His Tyr Thr Pro
    50                  55                  60

Ile Arg Thr Tyr Gln Val Cys Asn Val Met Asp His Ser Gln Asn Asn
65                  70                  75                  80

Trp Leu Arg Thr Asn Trp Val Pro Arg Asn Ser Ala Gln Lys Ile Tyr
                85                  90                  95

Val Glu Leu Lys Phe Thr Leu Arg Asp Cys Asn Ser Ile Pro Leu Val
            100                 105                 110

Leu Gly Thr Cys Lys Glu Thr Phe Asn Leu Tyr Tyr Met Glu Ser Asp
        115                 120                 125

Asp Asp His Gly Val Lys Phe Arg Glu His Gln Phe Thr Lys Ile Asp
    130                 135                 140

Thr Ile Ala Ala Asp Glu Ser Phe Thr Gln Met Asp Leu Gly Asp Arg
145                 150                 155                 160

Ile Leu Lys Leu Asn Thr Glu Ile Arg Glu Val Gly Pro Val Asn Lys
                165                 170                 175

Lys Gly Phe Tyr Leu Ala Phe Gln Asp Val Gly Ala Cys Val Ala Leu
            180                 185                 190

Val Ser Val Arg Val Tyr Phe Lys Lys Cys Pro Phe Thr Val Lys Asn
        195                 200                 205

Leu Ala Met Phe Pro Asp Thr Val Pro Met Asp Ser Gln Ser Leu Val
    210                 215                 220

Glu Val Arg Gly Ser Cys Val Asn Asn Ser Lys Glu Glu Asp Pro Pro
225                 230                 235                 240

Arg Met Tyr Cys Ser Thr Glu Gly Glu Trp Leu Val Pro Ile Gly Lys
                245                 250                 255

Cys Ser Cys Asn Ala Gly Tyr Glu Glu Arg Gly Phe Met Cys Gln
            260                 265                 270

<210> SEQ ID NO 5
<211> LENGTH: 813
<212> TYPE: DNA
<213> ORGANISM: Homo sapiens
```

```
<220> FEATURE:
<221> NAME/KEY: exon
<222> LOCATION: (1)..(813)
<223> OTHER INFORMATION: Exons I, II and III of HEK gene

<400> SEQUENCE: 5 atg gat tgt cag ctc tcc atc ctc ctc ctt ctc agc tgc tct gtt ctc       48 gac agc ttc ggg gaa ctg att ccg cag cct tcc aat gaa gtc aat cta       96 ctg gat tca aaa aca att caa ggg gag ctg ggc tgg atc tct tat cca      144 tca cat ggg tgg gaa gag atc agt ggt gtg gat gaa cat tac aca ccc      192 atc agg act tac cag gtg tgc aat gtc atg gac cac agt caa aac aat      240 tgg ctg aga aca aac tgg gtc ccc agg aac tca gct cag aag att tat      288 gtg gag ctc aag ttc act cta cga gac tgc aat agc att cca ttg gtt      336 tta gga act tgc aag gag aca ttc aac ctg tac tac atg gag tct gat      384 gat gat cat ggg gtg aaa ttt cga gag cat cag ttt aca aag att gac      432 acc att gca gct gat gaa agt ttc act caa atg gat ctt ggg gac cgt      480 att ctg aag ctc aac act gag att aga gaa gta ggt cct gtc aac aag      528 aag gga ttt tat ttg gca ttt caa gat gtt ggt gct tgt gtt gcc ttg      576 gtg tct gtg aga gta tac ttc aaa aag tgc cca ttt aca gtg aag aat      624 ctg gct atg ttt cca gac acg gta ccc atg gac tcc cag tcc ctg gtg      672 gag gtt aga ggg tct tgt gtc aac aat tct aag gag gaa gat cct cca      720 agg atg tac tgc agt aca gaa ggc gaa tgg ctt gta ccc att ggc aag      768 tgt tcc tgc aat gct ggc tat gaa gaa aga ggt ttt atg tgc caa          813

<210> SEQ ID NO 6
<211> LENGTH: 87
<212> TYPE: DNA
<213> ORGANISM: Homo sapiens
<220> FEATURE:
<221> NAME/KEY: exon
<222> LOCATION: (1)..(87)
<223> OTHER INFORMATION: Exon I of HEK gene

<400> SEQUENCE: 6 atg gat tgt cag ctc tcc atc ctc ctc ctt ctc agc tgc tct gtt ctc       48 gac agc ttc ggg gaa ctg att ccg cag cct tcc aat gaa                    87

<210> SEQ ID NO 7
<211> LENGTH: 66
<212> TYPE: DNA
<213> ORGANISM: Homo sapiens
<220> FEATURE:
<221> NAME/KEY: exon
<222> LOCATION: (1)..(66)
<223> OTHER INFORMATION: Exon II of HEK gene

<400> SEQUENCE: 7 gtc aat cta ctg gat tca aaa aca att caa ggg gag ctg ggc tgg atc       48 tct tat cca tca cat ggg                                                66

<210> SEQ ID NO 8
<211> LENGTH: 660
<212> TYPE: DNA
<213> ORGANISM: Homo sapiens
<220> FEATURE:
```

```
<221> NAME/KEY: exon
<222> LOCATION: (1)..(660)
<223> OTHER INFORMATION: Exon III of HEK gene

<400> SEQUENCE: 8 tgg gaa gag atc agt ggt gtg gat gaa cat tac aca ccc atc agg act      48 tac cag gtg tgc aat gtc atg gac cac agt caa aac aat tgg ctg aga      96 aca aac tgg gtc ccc agg aac tca gct cag aag att tat gtg gag ctc     144 aag ttc act cta cga gac tgc aat agc att cca ttg gtt tta gga act     192 tgc aag gag aca ttc aac ctg tac tac atg gag tct gat gat gat cat     240 ggg gtg aaa ttt cga gag cat cag ttt aca aag att gac acc att gca     288 gct gat gaa agt ttc act caa atg gat ctt ggg gac cgt att ctg aag     336 ctc aac act gag att aga gaa gta ggt cct gtc aac aag aag gga ttt     384 tat ttg gca ttt caa gat gtt ggt gct tgt gtt gcc ttg gtg tct gtg     432 aga gta tac ttc aaa aag tgc cca ttt aca gtg aag aat ctg gct atg     480 ttt cca gac acg gta ccc atg gac tcc cag tcc ctg gtg gag gtt aga     528 ggg tct tgt gtc aac aat tct aag gag gaa gat cct cca agg atg tac     576 tgc agt aca gaa ggc gaa tgg ctt gta ccc att ggc aag tgt tcc tgc     624 aat gct ggc tat gaa gaa aga ggt ttt atg tgc caa                     660

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 9
gtaggaattc ctctcactgc cctctgc                                        27

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 10
gtagggatcc ggcctcctgt tccag                                          25

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 11
gtaggaattc catggcttgt acccgac                                        27

<210> SEQ ID NO 12
<211> LENGTH: 27
<212> TYPE: DNA
<213> ORGANISM: Artificial Sequence
<220> FEATURE:
```

<223> OTHER INFORMATION: Description of Artificial Sequence: HEK PCR
      primer

<400> SEQUENCE: 12
gtagggatcc cataatgctt gcttctc                                       27

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 13
atggatggta acttctccag                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 14
tcattggaag gctgcggaat                                               20

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 15
gtagtctaga caagcttgtc gaccaggttt                                    30

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 16
gtagtctaga tcaagcctga ttagttgtga tgc                                33

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Eph family
      RTK degenerate  PCR primer

<400> SEQUENCE: 17
gtaggcatgc aaggagacmt tyaacc                                        26

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Eph family

```
                    RTK degenerate PCR primer

<400> SEQUENCE: 18
ccratgggna ccagccaytc                                              20

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 19
gtagtctaga gaactgattc cgcagccttc caa                               33

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 20
gtagtctaga tcatggaggt cgggtacaag c                                 31

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 21
gtagtctaga tcaagcttgg cacataaaac ctc                               33

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 22
gtagtctaga caagcttgtc gaccaggttt c                                 31

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: HEK PCR
      primer

<400> SEQUENCE: 23
gtagtctaga tcattggcta ctttcaccag ag                                32

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: LERK7 PCR
      primer
```

<400> SEQUENCE: 24
gtagtctaga caggacccgg gctccaaggc                                    30

<210> SEQ ID NO 25
<211> LENGTH: 7
<212> TYPE: PRT
<213> ORGANISM: Homo sapiens

<400> SEQUENCE: 25

Gln Asp Pro Gly Ser Lys Ala
 1               5